US006869924B1

(12) United States Patent
Yoshimura et al.

(10) Patent No.: US 6,869,924 B1
(45) Date of Patent: Mar. 22, 2005

(54) HUMAN DERIVED MONOCYTE ATTRACTING PURIFIED PROTEIN PRODUCT USEFUL IN A METHOD OF TREATING INFECTION AND NEOPLASMS IN A HUMAN BODY, AND THE CLONING OF FULL LENGTH CDNA THEREOF

(75) Inventors: Teizo Yoshimura, Frederick, MD (US); Elizabeth A. Robinson, Bethesda, MD (US); Ettore Appella, Chevy Chase, MD (US); Edward J. Leonard, Chevy Chase, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1826 days.

(21) Appl. No.: 07/330,446

(22) Filed: Mar. 30, 1989

Related U.S. Application Data

(63) Continuation-in-part of application No. 07/304,234, filed on Jan. 31, 1989, now abandoned.

(51) Int. Cl.$^7$ .............................................. C07K 14/00
(52) U.S. Cl. .......................... 514/2; 530/300; 530/324; 530/351; 530/344
(58) Field of Search ................................ 530/300, 324, 530/351, 344; 514/2, 12; 435/69.1, 69.5, 320.1; 935/18, 27, 33

(56) References Cited

U.S. PATENT DOCUMENTS

| 5,179,078 A | 1/1993 | Rollins et al. | 514/2 |
| 5,278,287 A | 1/1994 | Rollins et al. | 530/351 |
| 5,459,128 A | 10/1995 | Rollins et al. | 514/8 |

OTHER PUBLICATIONS

Ramb, Christine, et al. *Molecular Immunology*. 20(3):325–332. (1983).*

Valente, Anthony J., et al. *Biochemistry*. 72:4162–4168. (1988).*

Yoshimura, Teizo, et al. *Journal of Immunology* 142:1956–1962 (1989).*

Yoshimura et. al, The Journal of Immunology, vol. 142, pp. 1956–1962, No. 6, (Mar. 1989).

D.T.Graves et al,Science, vol. 245, pp. 1490–1493 (1989).

Ramb et al, Molecular Immunology, vol. 20(3), pp. 325–332, (Mar. 1983).

Valente et al, Biochemistry, vol. 27(II), pp. 4162–4168, 1988.

FEBS Letters, vol. 244, p. 487–493 (1989) by T. Yoshimura et al Human Monocyte Chemoattractant Protein–1 (MCP–1).

Furutani et al., *Biochemical and Biophysical Research Communications*, vol. 159, No. 1, pp. 249–255 (1989).

Altman et al, Jour. of Immunology, vol. 110, No. 3, pp. 801–810 (Mar. 1973).

K.A. Foon et al, Jour. of Immunology, vol. 117, No. 1, pp. 1545–1552(Nov. 1976).

Patent Abstracts of Japan, vol. 10, No. 71(C–334) (2128).

Poncz et al, Blood, vol. 69, No. 1, pp. 219–223 (Jan. 1987).

* cited by examiner

*Primary Examiner*—Karen Cochrane Carlson
(74) *Attorney, Agent, or Firm*—Merchant & Gould P.C.

(57) ABSTRACT

Pure peptide products, derived from either human glioma cell line U-105MG or human peripheral blood mononuclear leukocytes are provided; the products have a molecular mass of about 8,400 daltons, and the products exhibit optimal monocyte chemotactic activity at a concentration of 1 nM. The cloning of full length cDNA for the peptide products is also provided, as well as recombinant methods for the production of monocyte chemoattractant products. Methods of treating infection and neoplasms in a human body with such peptides and monocyte chemoattractant products are additionally provided, as well as pharmaceutical compositions for the same.

12 Claims, 7 Drawing Sheets

FIGURE 2

```
                                              -60         -50         -40         -30         -20         -10    -1
                                       CTAACCCAGAAACATCCAATTCTCAAACTGAAGCTCGCACTCTCGCCTCCAGC 10          20          30          40          50          60
ATG AAA GTC TCT GCC GCC CTT CTG CTG CTC ATA GCA GCC ACC TTC ATT CCC CAA
Met Lys Val Ser Ala Ala Leu Leu Leu Cys Leu Leu Ile Ala Ala Thr Phe Ile Pro Gln 70          80          90         100         110         120
GGG CTC GCT CAG CCA GAT GCA ATC AAT GCC CCA GTC ACC TGC TGT TAT AAC TTC ACC AAT
Gly Leu Ala Gln Pro Asp Ala Ile Asn Ala Pro Val Thr Cys Cys Tyr Asn Phe Thr Asn
               130
      130         140         150         160         170         180
AGG AAG ATC TCA GTG CAG AGG CTC GCG AGC TAT AGA AGA ATC TGT GCT GAC CCC AAG CAG
Arg Lys Ile Ser Val Gln Arg Leu Ala Ser Tyr Arg Arg Ile Cys Ala Asp Pro Lys Gln 190         200         210         220         230         240
AAA GAA GCT GTG ATC TTC AAG ACC ATT GTG GCC AAG GAG ATC TGT GCT GAC CCC AAG CAG
Lys Glu Ala Val Ile Phe Lys Thr Ile Val Ala Lys Glu Ile Cys Ala Asp Pro Lys Gln 250         260         270         280         290         300
AAG TGG GTT CAG GAT TCC ATG GAC CAC CTG GAC AAG CAA ACC CAA ACT CCG AAG ACT TGA
Lys Trp Val Gln Asp Ser Met Asp His Leu Asp Lys Gln Thr Gln Thr Pro Lys Thr 310         320         330         340         350         360         370         38
ACACTCACTCCACAACCCAAGAATCTGCAGCTAACTTATTTCCCCTAGCTTCCCCAGACACCCTGTTTTATTTTATT 0         390         400         410         420         430         440         450       4
ATAATGAATTTTGTTGTTGATGTGAAACATATATGCCTTAAGTAATGTAATTCTTATTTATTGATGTTTTAAG 60         470         480         490         500         510         520         530
TTTATCTTTCATGGTACTAGTGTTTTTAGATACAGAGACTTGGGGAAATTGCTTTTCCTCTTGAACCACAGTTCTACC 540         550         560         570         580         590         600         610
CCTGGGATGTTTTGAGGGTCTTTGCAAGAATCATTAATACAAAGAATTTTTTTACACATTCCAATGCATTGCTAAAATA 620         630         640         650         660         670         680
TTATTGTGGAAATGAATATTTTGTAACTATTACACACCAAATAATATTTTTGTACAAAAAAAAAAA
```

HUMAN DERIVED MONOCYTE ATTRACTING PURIFIED PROTEIN PRODUCT USEFUL IN A METHOD OF TREATING INFECTION AND NEOPLASMS IN A HUMAN BODY, AND THE CLONING OF FULL LENGTH CDNA THEREOF

CROSS REFERENCE TO RELATED APPLICATIONS

This application is a continuation-in-part of application Ser. No. 07/304,234 filed on Jan. 31, 1989 now abandoned.

BACKGROUND OF THE INVENTION

Macrophages play a central role in human immune responses and defense against infection. Macrophages originate from blood monocytes, which leave the circulation in response to several signals that are thought in include chemoattractants elaborated at foci of inflammation by tissue leukocytes stimulated by invading microorganisms or by tissue injury. Heretofore, no pure, human derived monocyte attracting substance has been provided.

SUMMARY OF THE INVENTION

The present invention is therefore concerned with providing human derived, purified, products that exhibit monocytic chemotactic activity (MCA). The invention is furthermore concerned with the method utilized to isolate and purify these peptide products, from human peripheral blood leukocytes and from a known human glioma cell line, and with the cloning of monocyte chemoattractant peptide full length cDNAs. The present invention is also concerned with a method of treating infection and neoplasms in a human body with monocyte chemoattractant peptide products disclosed herein, and with pharmaceutical compositions for these peptide products.

The present invention provides for:

A pure peptide product which may be derived from either (a) human glioma cell line U-105MG, or (b) human peripheral blood mononuclear leukocytes; said peptide product exhibiting optimal monocyte chemotactic activity at a concentration of 1 nM; said peptide product having an estimated molecular mass of about 8,400 daltons.

A pure peptide product, having a molecular mass of about 8,400 daltons, and exhibiting optimal monocyte chemotactic activity at a concentration of 1 nM, said purified peptide obtained by the process steps of:

(I) culturing live cells derived from:
(a) human glioma cell line U-105MG, or
(b) human peripheral blood mononuclear leukocytes, in an appropriate growth medium;

(II) separating said cells from said growth medium;

(III) chromatographing said growth medium on an Orange-A Sepharose column, utilizing an appropriate solvent, and collecting the fractions which contain the desired peptides;

(IV) chromatographing said peptide containing fractions obtained in Step III on an appropriate cation-exchange HPLC column, utilizing appropriate solvents, and collecting the fractions which contain said desired peptides;

(V) chromatographing said peptide containing fractions obtained in Step IV on a reverse phase HPLC column, utilizing an appropriate solvent, and collecting the fractions containing said desired peptides; and (VI) removing liquids from said peptide containing fractions obtained in Step V, to give said peptide product as a solid.

A method of preparing said purified peptide product, as outlined in steps I–VI above.

A pure peptide product, derived from glioma cell line U-105MG, said peptide product having an amino acid sequence of:

```
   1         10         20         30
XPDAINAPVTCCYNFTNRKISVQRLASYRRITSSKCPKE 40         50         60         70
AVIFKTIVAKEICADPKQKWVQDSMDHLDKQTQTPKT
```

Wherein
A is alanine;
C is cysteine;
D is aspartic acid;
E is glutamic acid;
F is phenylalanine;
H is histidine;
I is isoleucine;
K is lysine;
L is leucine;
M is methionine;
N is asparagine;
P is proline;
Q is glutamine;
R is arginine;
S is serine;
T is threonine;
V is valine;
W is tryptophan;
Y is tyrosine; and
X is pyrolutamic acid.

A cDNA coding for a human monocyte chemoattractant peptide.

A cDNA coding for a human monocyte chemoattractant peptide, comprising the following nucleotide sequence, or a bioequivalent thereof:

CAG CCA GAT GCA ATC AAT GCC CCA GTC ACC TGC TGT TAT AAC TTC ACC AAT AGG AAG ATC TCA GTG CAG AGG CTC GCG AGC TAT AGA AGA ATC ACC AGC AGC AAG TGT CCC AAA GAA GCT GTG ATC TTC AAG ACC ATT GTG GCC AAG GAG ATC TGT GCT GAC CCC AAG CAG AAG TGG GTT CAG GAT TCC ATG GAC CAC CTG GAC AAG CAA ACC CAA ACT CCG AAG ACT;

wherein C is cytosine, T is thymine, A is adenine, and G is guanine.

A cDNA coding for a human monocyte chemoattractant peptide, which chemoattractant peptide comprises the following amino acid sequence or a biological equivalent thereof:

Gln Pro Asp Ala Ile Asn Ala Pro Val Thr Cys Cys Tyr Asn Phe Thr Asn Arg Lys Ile Ser Val Gln Arg Leu Ala Ser Tyr Arg Arg Ile Thr Ser Ser Lys Cys Pro Lys Glu Ala Val Ile Phe Lys Thr Ile Val Ala Lys Glu Ile Cys Ala Asp Pro Lys Gln Lys Trp Val Gln Asp Ser Met Asp His Leu Asp Lys Gln Thr Gln Thr Pro Lys Thr;

wherein,
Gly is glycine, THR is threonine, ASN is asparagine,
Ala is alanine, Pro is proline, Gln is glutamine,
Val is valine, Asp is aspartic acid, Cys is cystein,
Ile is isoleucine, Glu is glutamic acid, Met is methionine,
Leu is leucine, Lys is lysine, Trp is tryptophan,
Ser is Serine, Arg is arginine, Phe is phenylalanine,
Tyr is tyrosine and His is histidine.

A method of treating infection in a human which method comprises administering to the site of an infection in a human, an effective infection treating amount of a purified peptide product, either genetically engineered, or derived from either: (a) human glioma cell line U-105MG, or (b) human peripheral blood mononuclear leukocytes; said peptide product exhibiting optimal monocytic chemotactic activity at a concentration of 1 nM: said peptide product having a molecular mass of about 8,400 daltons.

A method of treating neoplasms in a human, which method comprises administering to the site of a neoplasm in a human, an effective neoplasm treating amount of a purified peptide product, either genetically engineered, or derived from either (a) human glioma cell line U-105MG, or (b) human peripheral blood mononuclear leukocytes; said peptide product exhibiting optimal monocyte chemotactic activity at a concentration of 1 nM; said peptide product having a molecular mass of about 8,400 daltons.

A pharmaceutical composition comprising:

(I) a pure peptide product, either genetically engineered, or derived from either: (a) human glioma cell line U-105MG, or (b) human peripheral blood mononuclear leukocytes; said peptide product exhibiting optimal monocyte chemotactic activity at a concentration of 1 nM; said peptide product having an estimated molecular mass of about 8,400 daltons; and (II) a pharmaceutically acceptable carrier therefor.

The monocyte chemoattractant peptide of the present invention has been purified to substantial homogeneity. Thus, the term "pure" includes peptides which have been purified from various sources by removal of contaminating human proteins and other materials as well as peptides which have been synthesized or produced in a substantially pure state by methods provided herein, or by other methods. Preferably, the peptide of the present invention is at least 98% free of other proteins and peptides.

The term "Glioma cell line U-105MG" refers to a human derived cell line initiated by Pouten, J., and MacIntyre, E., "Long term culture of normal and neoplastic gliomas", *Acta Pathol. Microbiol. Scand.*, Vol. 74, p. 465 (1968). The cell line has been deposited with the American Type Culture Collection in Rockville, Md. in accordance with the Budapest Treaty on deposits as Deposit No. CRL 9932.

The terms "GDCF-1" and "GDCF-2" as used herein mean glioma derived chemotactic factors 1 and 2.

The terms "LDCF-1" and "LDCF-2" as used herein mean leukocyte derived chemotactic factors 1 and 2.

The term "MCP" as used herein includes MCP-1 and mutants and variants thereof, which are biologically equivalent to MCP-1. The term also includes the monocyte chemoattractant peptides hereinbefore labeled as GDCF-1, GDCF-2, LDCF-1 and LDCF-2, when the same are genetically engineered.

The term "MCP-1 cDNA" as used herein means the cDNA sequence illustrated in FIG. 2.

The term "MCP cDNA" as used herein means MCP-1 cDNA, and biologically equivalent mutants and variants thereof, including biologically active segments thereof.

The term "MCP-1" as used herein means human monocyte chemoattractant protein-1 having the amino acid sequence illustrated in FIG. 1.

The term "MCA" as used herein refers to monocyte chemotactic activity as determined by an in vitro assay in a multiwell chemotaxis chamber.

The terms "Unit of monocyte chemotactic activity" means the reciprocal of dilution causing 50% of the maximal chemotactic response.

The term "nM" as used herein means nanomole, i.e., $10^{-9}$ mole.

The term "MNL" as used herein means mononuclear leukocyte.

The term "PHA" as used herein means phytohemagglutinin.

The term "appropriate growth medium" as used herein includes RPMI 1640 medium containing 10% fetal calf serum.

The term "appropriate solvent" as used herein refers to aqueous solutions of alkali earth metal salts, such as sodium chloride and the like, when used in conjunction with chromatographing on an Orange-A Sepharose column and cation-exchange HPLC columns; and to organic solvent mixtures for use with reverse phase HPLC columns.

The term "pharmaceutically acceptable carrier" as used herein refers to conventional pharmaceutic excipients or additives used in the pharmaceutical manufacturing art, and necessarily includes while not limited to, those excipients or additives contained herein under the caption "Pharmaceutical Compositions".

The term "unit dosage form" as used herein refers to physically discrete units suitable as unitary dosages for human and animal subjects, each unit containing a predetermined quantity of either a purified peptide product, MCP or MCP-1, calculated in an amount suficient to produce the desired effect in association with a pharmaceutically acceptable diluent, carrier or vehicle. The specifications for the novel unit dosage forms of the present invention depend on the particular polypeptide employed and the effect to be achieved, and the pharmacodynamics associated with each compound in the host.

"The term "LAMBDA ZAP II®" as used herein refers to a commercially available general purpose lambda cloning vector with automatic in vivo excision of plasmids subclones containing as cloning sites EcoR I, Not I, Xba I, Spe I, Xho I and Sac I, and which is capable of accepting an insert with a size of 0 to 10 Kb. LAMBDA ZAP II® is commercially available from STRATAGENE, 11099 North Torrey Pines Road, La Jolla, Calif. 92037."

BRIEF DESCRIPTION OF THE DRAWINGS

FIG. 2. Nucleotide sequence of human MCP-1. Triangle: N-terminus of mature MCP-1. Dashed line: potential N-linked glycosylation site. Solid line: sequence used for oligonucleotide probe construction. Dotted line: polyadenylation signal.

DETAILED DESCRIPTION OF THE INVENTION

Figure 1:
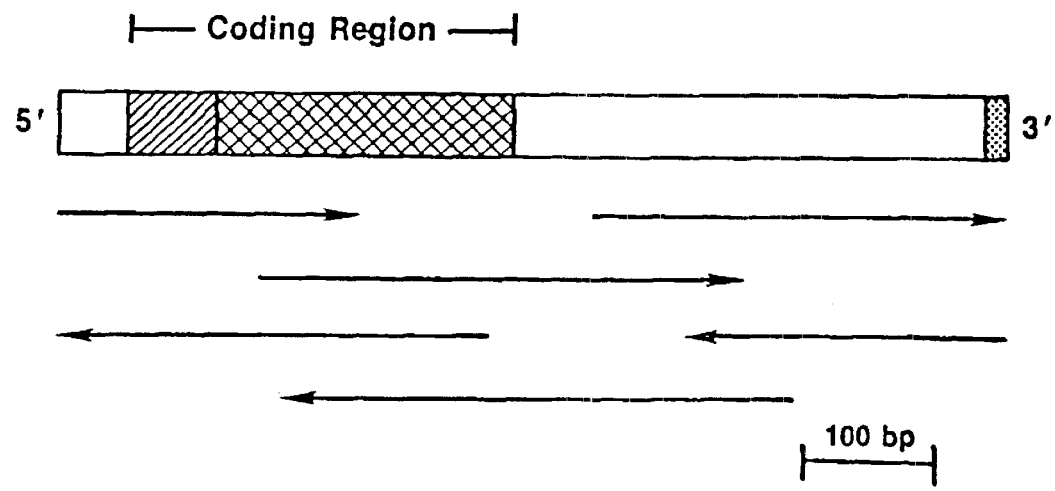
FIG. 1. A. Amino acid sequence of a portion of a peptide fragment of a *S. aureus* VB protease digest of MCP-1. B. Probes based on the above sequence. C. Structural organization and sequencing strategy of human MCP-1 cDNA. Arrows show direction and extend of determined sequences. Cross-hatched area indicates the coding region for the mature form of MCP-1. Dotted region indicates poly(A).

The following description is meant to aid those skilled in the art in practicing the present invention. The examples which follow should be considered as integral to this description, and therefore it is to be regarded as advantageous that one practicing the present invention, review the Examples contained herein in conjunction with this detailed description. Furthermore, it is noted that when one is practicing the present invention, or simply reading the present disclosure, it should be understood that certain terms such as peptide, polypeptide and protein can be used interchangably, and as well that the terms MCP, MCP-1, GDCF-1, GDCF-2, LDCF-1 and LDCF-2 can at times be used interchangably, such as in recombinant synthesis methods provided for MCP and MCP-1 herein.

Methods for the isolation and purification of human monocyte chemoattractant factor from human glioma cell line U-105MG is provided in detail in Example (I) below, as is the isolation and purification of monocyte chemoattractant factor from human peripheral blood leukocytes in Example (II) below. Furthermore, Example (III) below provides a detailed explanation as to the amino acid sequencing of human monocyte chemoattractant factor. Example (IV) below, provides for the cloning and coding of human monocyte chemoattractant protein-1 cDNA (MCP-1 cDNA) which contains a gene responsible for synthesis of human monocyte chemoattractant factor.

Example (V) below, provides for the treatment of infection with monocyte chemoattractant factor, and Example (VI) provides for the treatment of neoplasts with monocyte chemoattractant factor.

Example (VII) provides for a method of inhibiting the actions of monocyte chemoattractant factor in vivo.

The degree of amino acid sequence homology with MCP-1 which brings a protein within the scope of the definition of monocyte chemoattractant protein (MCP) herein will vary depending upon whether the homology between the candidate protein and MCP-1 falls within or without the MCP-1 regions responsible for monocyte chemoattractant activity; domains which are critical for monocyte chemoattractant activity should exhibit a high degree of homology in order to fall within the definition, while sequences not involved in maintaining MPC-1 conformation or in effecting receptor binding may show comparatively low homology. In addition, critical domains may exhibit monocyte chemoattractant activity and yet remain homologous as defined herein if residues containing functionally similar amino acid side chains are substituted. Functionally similar refers to dominant characteristics of the side chains such as basic, neutral or acid, or the presence or absence of steric bulk.

Generally, a protein defined as MCP will contain regions substantially homologous with the FIG. 2 protein or fragments thereof over a continuous block of from about at least 70 amino acid residues, in particular the blocks encompassed by residues 23–99 in FIG. 2.

It is important to observe that any characteristics such as molecular weight or the like, for the native or wild type mature human MCP-1 of FIG. 2 obtained from peripheral lymphocyte or established cell line cultures are descriptive only for the native species of MCP-1. MCP, however, as contemplated by the definition provided herein also includes other species which may not exhibit all of the characteristics of native MCP-1. While MCP as defined herein includes native MCP-1, other related proteins can fall within the definition as well. For example, MCP-1 derivatives like insertion mutants, deletion mutants, or fusion proteins may produce MCP outside of a molecular weight established for native human MCP-1 (fusion proteins with mature MCP-1 or MCP-1 itself as well as insertion mutants will have a greater molecular weight than native, mature MCP-1, while deletion mutants of native, mature MCP-1 will have a lower molecular weight). Similarly, an MCP may be engineered in order to reduce or eliminate susceptibility to hydrolysis by trypsin or other proteases.

Note also that the language "biological equivalent" or "bioequivalent" as used herein also includes MCP proteins which can be converted, as by enzymatic hydrolysis, from an inactive state analogous to a zymogen to a protein fragment which exhibits the desired biological activity. Typically, inactive precursors will be fusion proteins in which mature MCP-1 is linked by a peptide bond at its carboxyl terminus to a human protein or fragment thereof. The sequence at this peptide bond or nearby is selected so as to be susceptible to proteolytic hydrolysis to release MCP or MCP-1, either in vivo or, as part of a manufacturing protocol, in vitro. MCP that is so generated then will exhibit monocyte chemoattractant activity.

While MCP ordinarily is meant to mean human MCP, MCP from sources such as other primates, or from such sources as murine, porcine, equine or bovine is also considered included within the definition of MCP above, so long as it meets the standards described above for homologous regions and monocyte chemoattractant activity.

MCP also includes multimeric forms, and multimers are accordingly envisioned as suitable for use in in vivo therapy. While it is thought desirable to express and recover MCP as a substantially homogeneous multimer or monomer, MCP may be used therapeutically as a mixture of different multimers.

Derivatives of MCP-1 are also included within the scope of the term MCP. Such derivatives include, for example, amino acid sequence mutants, glycosylation variants and covalent or aggregative conjugates with other chemical moieties. Covalent derivatives would generally be prepared by linkage of functionalities to groups which are found in the MCP-1 amino acid side chains or at the N- or c-termini, by means known in the art. These derivatives may, for example, include: aliphatic esters or amides of the carboxyl terminus or residues containing carboxyl side chains, O-acyl derivatives of hydroxyl group-containing residues, N-acyl derivatives of the amino terminal amino acid or amino-group containing residues.

MCP-1 or MCP should preferably be synthesized in cultures of recombinant organisms. Neither peripheral blood lymphocytes (PBLs) nor cell lines are the most desirable (even though such are utilized in Examples I and II herein). Since it is difficult in practice to obtain PBLs of one class which are free of contamination by cells of other classes, e.g. to obtain macrophages free of B or T cells. Such contamination renders the separation procedure applied to the products of such cells difficult because of other potential protein release by contaminant cells. Furthermore, MCP obtained from nonrecombinant culture is expensive and consists solely of native MCP-1, such cultures thereby lacking in the flexibility of recombinant culture to improve upon the characteristics of MCP-1.

Alternatively, and preferably, MCP may be synthesized in host cells transformed with vectors containing DNA encoding MCP-1 or more generally MCP. A vector is a replicable DNA construct. Vectors may be used either to amplify DNA encoding MCP and/or to express DNA which encodes MCP. An expression vector is a replicable DNA construct in which a DNA sequence encoding MCP is operably linked to suitable control sequences capable of effecting the expression of MCP in a suitable host. Such control sequences include a transcriptional promoter, an optional operator sequence to control transcription, a sequence encoding suitable mRNA ribosomal binding sites, and sequences which control termination of transcription and translation.

DNA which encodes MCP-1 is obtained by chemical synthesis, by screening reverse transcripts of mRNA from PBL (purified blood leukocytes) or cell line cultures. Some suitable cell line for culture are U-105MG, U-373MG and KMG-5.

This DNA is covalently labelled with a detectable substance such as a fluorescent group, a radioactive atom or a chemiluminescent group by methods known per se and including fluorescent labeled probes as utilized in Example IV below. The DNA is then used in conventional hybridization assays. Such assays are employed in identifying appropriate MCP vectors and transformants.

However, if one desires to culture MCP-1, without utilizing recombinant DNA technology, then MCP synthesizing cells of U-105MG (or other appropriate cell line) can be initially cultured in conventional fashion until reaching a density of about $8-12 \times 10^5$ cells/ml. The cells can then be transferred to a serum-free medium and grown until a desired concentration of MCP-1 has accumulated in the culture medium. Thereafter the culture supernatant may be clarified by centrifugation or other means of separating cell debris from the soluble components. Centrifugation should be carried out at low speed so as to move only suspended particles. The supernatant is then purified as described in either Examples I or II below.

Suitable vectors comprise plasmids, viruses (including phage), and integratable DNA fragments (i.e., integratable into the host genome by recombination). Once it has transformed a suitable host, the vector should replicate and function independently of the host genome, or may, in some instances, integrate into the genome itself. In the present specification, "vector" is generic to "plasmid"; but plasmids are the most commonly used form of vector at present. However, all other forms of vectors which serve an equivalent function and which are, or become, known in the art are suitable for use herein. Suitable vectors will contain replicon and control sequences which are derived from species compatible with the intended expression host. Transformed host cells are cells which have been transformed or transfected with an MCP vector constructed using recombinant DNA techniques. Transformed host cells should ordinarily express MCP. Thus, the expressed MCP would be deposited intracellularly or secreted into either the periplasmic space or the culture supernatant, depending upon the host cell selected.

DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means continuous and, in the case of secretory leaders, contiguous and in reading phase.

Suitable host cells are thought to be prokaryotes, yeast or higher eukaryotic cells. Prokaryotes include gram negative or gram positive organisms, for example, *E. coli* or *Bacilli*. Higher eukaryotic cells also include established cell lines of mammalian origin as described below. A preferred host cell could be phage-resistant *E. coli* or M13 mp19, although other prokaryotes could also be suitable.

Prokaryotic host-vector systems are also thought preferred for the expression of MCP-1, and plethora of suitable microbial vectors are available. Generally, a microbial vector would contain an origin of replication recognized by the intended host, a promoter which would function in the host and a phenotypic selection gene, for example a gene encoding proteins conferring antibiotic resistance or supplying an auxotrophic requirement. Similar constructs could be manufactured for other hosts. For example, *E. coli* is typically transformed using pBR322, a plasmid derived from an *E. coli* species (Bolivar, et al., 1977, "Gene" 2: 95). pBR322 contains genes for ampicillin and tetracycline resistance and thus provides easy means for identifying transformed cells.

Vectors must contain a promoter which is recognized by the host organism. This is generally a promoter homologous to the intended host. Promoters most commonly used in recombinant DNA construction include the B-lactamase (penicillinase) and lactose promoter systems (Chang et al., 1978, "Nature", 275: 615; and Goeddel et al., 1979, "Nature", 281: 544), a tryptophan (trp) promoter system (Goeddel et al., 1980, "Nucleic Acids Res." 8: 4057 and EPO App. Publ. No. 36,776) and the tac promoter [H. De Boer et al., "Proc. Nat'l. Acad. Sci. U.S.A." 80: 21–25 (1983)]. While these are the most commonly used, other known microbial promoters could also be suitable.

MCP initially is recovered from cultures. Transformed nonsecreting cells are lysed by sonication or other acceptable method and debris separated by centrifugation, while the supernatants from secreting cells (such as induced cell lines) are simply separated from the cells by centrifugation.

Purification of monocyte chemoattractant from the supernatant liquid can generally be had by purification methods provided herein for purification of monocyte chemoattractant peptide in Examples (I) and (II) wherein monocyte chemoattractant is isolated and purified from cells.

The following Examples serve to further illustrate the present invention; but the same should not be construed as limiting to the scope of the invention disclosed herein.

EXAMPLE I

Purification of Monocyte Attracting Peptides from Human Glioma Cell Line U-105MG Materials and Methods Cell Culture Human glioma cell line U-105MG was utilized. Cells were cultured in 150 $cm^2$ tissue culture flasks (Costar, Cambridge, Mass.) in RPMI 1640 medium (Advanced Biotechnologies Inc., Silver Spring, Md.) supplemented with 10% fetal bovine serum (FBS, HyClone, Logan, Utah), 20 mM L-glutamine and 50 $\mu$g/ml gentamycin. When cells became confluent, medium was replaced with 100 ml of FBS-free RPMI 1640 medium, which was collected 4 days later and frozen at $-20°$ C.

Dye-Ligand Chromatography

Four liters of above obtained cultured fluid were concentrated to 50 ml on a 150 mm diameter Amicon Diaflo membrane (YM-5, molecular weight cutoff 5,000), dialyzed against 20 mM tris-HCl, pH 8.0, and applied on a column of orange-A Sepharose (1×5 cm, Amicon Corp., Danvers, Mass.) that was equilibrated with the same buffer. The column was eluted with a linear NaCl gradient (limit 0.6M) at a flow rate of 0.5 ml/min; 2 ml fractions were collected, and those with chemotactic activity were pooled.

Cation Exchange HPLC

The pool of active fractions eluted from Orange-A Sepharose was concentrated to 2 ml, dialyzed overnight at 4° C. against starting buffer (20 mM Mops, pH 6.5, in 0.1M NaCl) and applied to a 0.75×7.5 cm CM 3SW column (Toyo Soda, Tokyo) at room temperature. The column was eluted with a series of linear Nacl gradients (limit 20 mM Mops, pH 6.5, in 0.4M NaCl) at a flow rate of 1 ml/min. One ml fractions were collected and assayed for chemotactic activity. Two separate peaks were found.

Reverse Phase HPLC

Each of the active peaks from the cation exchange column was applied to a 0.5×25 cm Hi-Pore reverse phase column (BioRad, Richmond, Calif.), equilibrated with a starting solvent of 0.1% trifluoroacetic acid (TFA) in water. A linear gradient was programmed, with a limit buffer of 70% (v/v) acetonitrile in water containing 0.1% TFA. Flow rate was 1 ml/min; 1.0 ml fractions were collected, and those in the region of $A_{280}$ peaks were assayed for chemotactic activity.

Results

Glioma Cell Line U-105MG Derived Peptides (GDCF-1 AND GDCF-2)

Four liters of conditioned medium from U-105MG cells were concentrated to 50 ml, dialyzed against starting buffer and applied to an Orange-A Sepharose column. The column was eluted with a linear NaCl gradient. The bulk of the protein did not bind to the column, and emerged directly in the first 27 fractions. Chemotactic activity bound to the column and was eluted between 0.2M and 0.45M NaCl. As shown in Table 1, MCA was separated from about 98% of the conditioned medium protein, and recovery of chemotactic activity was 78%. Pooled active fractions were concentrated to 2 ml and applied to a CM-HPLC column. Chemotactic activity was recovered in two separate peaks that coeluted with two major $A_{280}$ peaks. Sequential fractions corresponding to the two MCA peaks were analyzed by SDS-PAGE. The first MCA peak (GDCF-1), which had maximal chemotactic activity in fractions 36 and 37, showed a major band with maximal intensity in these fractions. There was also a narrower band immediately about the major band, which could be seen in the lanes of fractions 35 and 36. The second MCA peak (GDCF-2), with maximal chemotactic activity in fractions 45 and 46, showed a single major band with peak intensity in these fractions. By reference to the mobility of protein standards, estimates of the molecular masses of GDCF-1 and -2 were 15 kDa and 13 kDa. For further purification, GDCF-1 (fraction 37) and GDCF-2 (fractions 45 and 46) were applied to reverse phase HPLC columns and eluted with a linear acetonitrile gradient. Each MCA peak coeluted with a single, sharp, $A_{226}$ peak. The presence, in the chromatograms of absorbance peaks without chemotactic activity showed that the reverse phase column removed residual extraneous protein. This is also shown in Table 1 by the increased specific activity of the RP-HPLC products. When RP-HPLC GDCF-1 and GDCF-2 were analyzed by SDS-PAGE, single bands were found, with estimated molecular masses of 15 kDa and 13 kDa, respectively. As summarized in Table 1, from 4 liters of conditioned medium, about 5 µg of GDCF-1 and 19 µg of GDCF-2 were purified to apparent homogeneity. Specific activity was 165 times that of the starting material for GDCF-1, and 150 times for GDCF-2. Total recovery was approximately 13%.

Amino Acid Analysis of GDCF-1 and GDCF-2

Table 2 shows the amino acid composition of purified GDCF-1 and -2, based on two separate analyses of each peptide. Within the limits of error of the method, the amino acid composition of the peptides is identical. A minimal molecular mass, calculated from the amino acid composition, is approximately 8400 daltons.

When N-terminal amino acid analysis was attempted, no degradation of either peptide occurred, suggesting that the N-terminus was blocked.

Assay of GDCF Chemotactic Activity for Monocytes and Neutrophils

For both peptides, about 35% of monocytes added to assay wells migrated at the optimal concentration of 1 nM. No significant neutrophil migration was observed over a GDCF concentration range of 0.01 to 30 nM in that experiment. Thus, showing GDCF attracts monocytes but not neutrophils.

Assay to Distinguish Chemotaxis from Chemokinesis

Purified GDCF was added in different concentrations to top and bottom wells of multiwell chambers, as outlined in Table 3. Dose-dependent monocyte migration was observed only when GDCF was in bottom wells. No significant migration occurred when top and bottom wells contained equal concentrations of GDCF, showing that migration was due primarily to chemotaxis, not chemokinesis.

Discussion of Results

Two chemotactic peptides for human monocytes, GDCF-1 and GDCF-2, were purified to apparent homogeneity from culture fluid of a human glioma cell line. Although these two peptides were separated into two completely distinct peaks by CM-HPLC chromatography, their elution patterns from a reverse phase HPLC column were identical; and their amino acid compositions were indistinguishable. Chemotactic potency and efficacy of both peptides were very similar (Table III); and both were chemotactic for monocytes but not neutrophils. It is possible that the two peptides differ only by post-translation modifications, such as phosphorylation, glycosylation or degradation. Based on the amino acid composition, our estimate of the molecular mass of GDCF is 8400 daltons, which is considerably less than the 15 and 13 kDa values determined by SDS-PAGE for GDCF-1 and -2. Discrepancies between molecular mass estimates obtained by these different methods of biologically active peptides have been reported by others, e.g., Richmond, A., et al., *Embo. J.*, Vol. 7, p. 2025–33 (1988).

As shown in the last column of Table 2, purification of GDCF to homogeneity was associated with only a 150-fold increase in specific activity, which reflects the relatively high concentration of GDCF in U-105MG glioma cell culture fluid. This is due to the absence of fetal bovine serum in the medium, and also indicates that GDCF represents a significant percentage of the proteins secreted by the U-105MG cell line.

The amino acid composition of GDCF is different from other cytokines that have been reported to be chemotactic for monocytes including IL-1, TNF, GM-CSF, M-CSF and TGF-beta. GDCF is also distinct from other cytokines produced by glioma cells, including IL-1 and platelet-derived growth factor.

Summary of Results

Two chemoattractants for human monocytes were purified to apparent homogeneity from the culture supernatant of a glioma cell line (U-105MG) by sequential chromatography on Orange-A Sepharose, an HPLC cation exchanger and a reverse phase HPLC column. On SDS-PAGE gels under reducing or non-reducing conditions, the molecular masses of the two peptides (GDCF-1 and GDCF-2) were 15 and 13 kDa, respectively. Amino acid composition of these molecules was almost identical, and differed from other cytokines that have been reported. The N-terminus of each peptide was apparently blocked. When tested for chemotactic efficacy, the peptides attracted approximately 30% of the monocytes added to chemotaxis chambers, at the optimal concentration of $10^{-9}$M. The activity was chemotactic rather than chemokinetic. In contrast to their interaction with human monocytes, the pure peptides did not attract neutrophils.

EXAMPLE II

Purification of Monocyte Attracting Peptides from Human Peripheral Blood Leukocytes Cell Culture Human peripheral blood mononuclear leukocytes (MNL's) were isolated by metrizoate/Ficoll (Accurate Chemical and Scientific Corp., Westbury, N.Y.) density sedimentation of leukapheresis preparations obtained by the Blood Bank, Clinical Center, NIH, from healthy human donors. Cells were washed three times with isotonic phosphate buffered saline and resuspended in RPMI 1640 culture medium (Advanced Biotechnologies, Inc., Silver Spring, Md.) supplemented with 2 mM glutamine and 50 $\mu$g/ml gentamycin. Cells were cultured at a concentration of $5 \times 10^6$ cells per ml in tissue culture flasks with 2.5 $\mu$g/ml phytohemagglutin (PHA) (Sigma, St. Louis, Mo.). After incubation for 24 to 40 hrs, cells were harvested; cell-free conditioned medium was obtained by centrifugation at 400×g for 10 min.

Dye-Ligand Affinity Chromatography

For large scale purification, 4 liters of PHA culture supernatant were concentrated to about 40 ml on a 150 mm diameter Amicon Diaflo YM-5 membrane (m.w. cutoff 5000), dialyzed against 20 mM tris-HCl, pH 8.0, and applied on a 1×5 cm column of Orange-A Sepharose (Amicon Corp., Danvers, Mass.) equilibrated with the same buffer. The column was eluted at a flow rate of 0.5 ml/min with a linear NaCl gradient to a limit of 0.6M in the same buffer. Fractions were collected and analyzed for monocytic chemotactic activity—thus indicating presence of a desired peptide.

High Pressure Liquid Chromatography Gel Filtration

Fractions containing peptides from the previous step were utilized, and HPLC gel filtration was performed at room temperature on a 7.5×600 mm TSK-2000 column (Toyo Soda, Tokyo, Japan), equilibrated with phosphate buffered saline, pH 7.4. Fractions of 0.5 ml were collected at a flow rate of 1 ml/min. The column was calibrated with bovine serum albumin (BSA), ovalbumin (OVA), chymotrypsinogen A, cytochrome c, and aprotinin. Fractions were collected and analyzed for MCA properties.

HPLC Chromatofocusing

Chromatofocusing was performed on a Mono P HR5/20 FPLC column (Pharmacia LKB Biotechnology Inc., Piscataway, N.J.). Two pH ranges were chosen, pH 7–4 and 9–6. For the 7–4 pH gradient, starting buffer was 25 mM bis-tris, pH 7.1, and the column was eluted with 10% (v/v) Polybuffer 74, pH 4.0. For pH range 9–6, 25 mM diethanolamine, pH 9.5, and 10% (v/v) Polybuffer 96, pH 6.0 were used. MCA obtained from 8 gel filtration runs on TSK-2000 was concentrated to 5 ml, and a 2 ml aliquot was dialyzed against starting buffer in a 3,500 mw cutoff dialysis bag (Spectrum Medical Industries Inc., Los Angeles, Calif.) and applied on a Mono P column. The column was eluted at a flow rate of 1 ml/min. Two ml fractions were collected; pH and chemotactic activity were determined.

Cation Exchange HPLC

The pool of fractions with chemotactic activity eluted from Orange-A Sepharose was concentrated and dialyzed against starting buffer (20 mM Mops, p 6.5, 0.1M NaCl), and applied on a 0.75×7.5 cm CM-3SW-column (Toyo Soda, Tokyo) at room temperature. The limit buffer was 20 mM Mops, pH 6.5, 0.4M NaCl. A series of linear gradients was programmed at a flow rate of 1.0 ml/min; 1.0 ml fractions were collected.

Reverse Phase HPLC

The pool of fractions eluted from the cation exchange column was applied to a 0.5×25 cm Hi-Pore reverse phase column (Bio-Rad, Richmond, Calif.) equilibrated with a starting solvent of 0.1% trifluoroacetic acid in water. A linear gradient was programmed, with a limit buffer of 70% (v/v) acetonitrile in water containing 0.1% trifluoroacetic acid. Flow rate was 1.0 ml/min; 1.0 ml fractions were collected and assayed for MCA properties.

SDS Page

Electrophoresis was carried out on a vertical slab gel of 15% acrylamide with a discontinuous tris glycine buffer system. Samples, as well as a solution of molecular weight standards, were mixed with equal volumes of double strength sample buffer (20% glycerol, 6% 2-mercaptoethanol), boiled, and applied to the gel. After electrophoresis at 12 mA for 3 hrs, the gel was stained with a silver staining kit (ICN Biomedicals, Irvine, Calif.).

Amino Acid Composition and Sequence Analysis

After a 24 hr hydrolysis in 6 M HCl in vacuo at 106° C., amino acid composition was determined on a Beckman System 6300 (Beckman Instruments, Fullerton, Calif.). N-terminal sequence analysis was performed on an Applied Biosystems 470A Protein Sequencer (Applied Biosystems, Foster City, Calif.).

Chemotaxis Assay

Mononuclear cells from human venous blood were separated by centrifugation on metrizoate/Ficoll and used for chemotaxis in multiwell chambers. Cell suspensions were added to upper wells of the chambers; they were separated from lower wells containing chemoattractant by a 10 $\mu$m thick polycarbonate membrane with 5 $\mu$m diameter holes. The number of monocytes that migrated through the holes to the attractant side of the membrane during a 90 min incubation was counted with an image analyzer. Results were expressed as the percentage of the input number of monocytes that migrated per well for duplicate wells. The reference chemoattractant fMet-Leu-Phe (Peninsula Laboratories, Belmont, Calif.) was dissolved in ethanol at a concentration of 1 mM and diluted for assay.

Results

Molecular Sieve Chromatography on an HPLC Column

One hundred ml of culture medium harvested 40 hr after addition of PHA to human MNL's was concentrated to 2 ml, and 200 $\mu$l was injected into a TASK-2000 column. Eluted fractions were assayed for chemotactic activity at 1:10 and 1:50 dilutions. As shown in FIG. 1, several peaks of chemotactic activity were detected at 1:10 dilution. At a 1:50 dilution, a single peak was seen, which represented about 40% of total applied activity. The center of this peak corresponded to a molecular mass of 17 kDa.

HPLC Chromatofocusing

The active fractions (34–40) from 8 runs on TSK-2000 were pooled and concentrated to 5 ml. Two ml aliquots of this material were used for chromatofocusing runs on a Mono P column. When pH range 7–4 was used, two major chemotactic activity peaks were seen, one in the pass through fractions and one at an early stage of the pH gradient. At pH range 9–6, a single broad activity peak was seen at pH 9.4 to 7.8, which represented about 85% of the applied activity. After the pH gradient was completed, an additional 15% of activity was eluted by 2M NaCl in fraction 34.

Affinity Chromatography on Orange-A Sepharose

Since human glioma cell derived monocyte chemotactic factor could bind to Orange-A Sepharose, the binding capacity of the leukocyte derived factor was studied. All of the 17 kDa, high pI chemotactic activity bound to Orange-A Sepharose, and was eluted by 0.5M NaCl.

Purification of the Basic 17 kDa Chemotactic Factor

Since the 17 kDa chemotactic factor in the culture supernatant of PHA-stimulated leukocytes behaved similarly to GDCF on TSK-2000, Mono P and Orange-A Sepharose, the purification of this factor was attempted by the same procedures as those for GDCF.

Four liters of PHA culture supernatant were concentrated to about 40 ml, dialyzed against starting buffer, and applied to an Orange-A Sepharose column. About 50% of the activity passed through the column without binding. This was not due to overloading, since activity was seen in very early fractions. The bound activity was eluted by NaCl (Table IV). Active fractions (40–56) were pooled, concentrated, dialyzed, and applied to a cation exchange column for further purification. By CM-HPLC chromatography, MCA was separated into two distinct peaks which were eluted in the middle of the NaCl gradient. Each of these peaks (fraction 39+40, fraction 49+50) was further purified on a RP-HPLC column. Each MCA peak coeluted with a sharp $A_{226}$ peak (fraction 40). The behavior of this leukocyte derived chemotactic activity on Orange-A Sepharose, CM-HPLC and RP-HPLC was very similar to that of GDCF. Therefore, the two chemotactic peptides purified from glioma cells (GDCF-1 and GDCF-2) and the two chemotactic peptides purified from PHA-stimulated MNL's (LDCF-1 and LDCF-2) were analyzed on a single SDS-PAGE gel. The migration positions of the two glioma-derived peptides were identical to the migration positions of the two MNL-derived peptides, suggesting that the chemotactic peptides from these different cell sources were identical.

Amino Acid Analysis

Table V shows that the amino acid composition of the two leukocyte-derived chemotactic peptides is almost identical. A minimal molecular mass, calculated from the amino acid composition, is approximately 8400 daltons. Within the limits of error of the method, the amino acid composition of LDCF is identical to that previously determined for GDCF.

When N-terminal amino acid analysis was attempted, no degradation of either peptide occurred, suggesting that the N-terminus was blocked.

Comparison of Chemotactic Activity for Monocytes and Neutrophils

Both peptides induced peak responses at $10^{-9}$M, at which about 30% of input cells migrated. The magnitude of the response to the two peptides was about the same as to fMet-Leu-Phe. Over the concentration range studied, neither peptide induced chemotaxis responses by human neutrophils.

Discussion of Results

Two peptides with chemotactic activity for human monocytes were purified to apparent homogeneity from PHA-stimulated MNL's. The two peptides eluted from a CM-HPLC column in different peaks, and by SDS-PAGE had molecular masses of 15 and 13 kDa. However, they had identical elution patterns by reverse phase HPLC, similar amino acid compositions, and both had an apparently blocked amino terminus. These similarities suggest that the two peptides are derived from the same gene and differ because of post-translational modifications. Such modifications might account for not only the different elution patterns of LDCF-1 and -2 on CM-HPLC, but also the discrepancy between the molecular mass estimates by SDS-PAGE and those calculated from amino acid composition, Tung, J., et al., *Biochem. Biophys. Res. Comm.*, Vol. 42, p. 1117 (1971). Similar discrepancies have been reported by others for peptides in the same size range, Richmond, et al., supra. In addition, it appears that the two derived leukocyte derived chemotactic peptide are indistinguishable from the glioma cell line U-105MG chemotactic peptides obtained herein in Example I.

EXAMPLE III

Amino Acid Sequencing of Glioma Cell Line U-150MG Derived Human Leukocyte Attracting Peptide (GDCF-2)

Materials and Methods

Purification of GDCF. Human glioma cell-derived monocyte chemotactic factors were purified from culture fluid of U-105MG cells by sequential chromatography on an Orange-A Sepharose column, a cation exchange column and a reverse-phase column as in Example I.

Chemical Modification of GDCF-2. GDCF-2 was fully reduced and carboxymethylated with iodo $[2-^3H]$acetic acid (Amersham, 131 Ci/mol) as described by Robinson et al, J. Biol. Chem., Vol. 254, p. 11418–11430 (1979). Radioactivity was measured with an Analytic 81 liquid scintillation counter; $^3H$ was counted with an efficiency of 44%. Carboxymethylated GDCF was succinylated in 4 M urea-0.4M bicene, pH 8.6 with a 100-fold excess (over amino groups) of succinic anhydride (Eastman).

Enzymatic Digestion and Peptide Purification.

Carboxymethylated GDCF-2 and a control peptide, Big Gastrin 1 (Sigma) with N-terminal pyroglutamic acid, were digested with calf liver pyroglutamate aminopeptidase (Boehringer-Mannheim) essentially as described by Podell, D., et al., *Biochem. Biophys. Res. Comm.*, Vol. 81, p. 176–85 (1978). Carboxymethylated GDCF-2 was digested at 37° C. in 50 mM $NH_4HCO_3$ with *S. aureus* protease V8 (Boehringer-Mannheim, 1/25, w/w) for 6 h, and with endoproteinase Asp-N (Boehringer-Mannheim 1/80, w/w) for 20 hr. Carboxymethylated, succinylated GDCF-2 was digested at 25° C. with trypsin (Worthington 1/50 w/w) for 20 hr.

Each digest was subjected to automated Edman degradation (as a mixture) before fractionation by HPLC. Peptides were purified by HPLC using a Hewlett Packard 1090A Liquid Chromatograph and Ultrapore RPSC C-3 or C-8 columns (Beckman) or an Applied Biosystems Model 130A and an RP300 Aquapore column (Applied Biosystems). Solvents were 0.10% trifluoroacetic acid in water (A) and acetonitrile (B), respectively.

Amino Acid Composition and Edman Degradation. Samples were hydrolyzed in vacuo in 6N HCl at 106° C. for 224 hr and analyzed on a Beckman System 6300. Edman degradation was performed on an Applied Biosystems 470A equipped with an on-line 120A PTH analyzer. PTH carboxymethylcysteine was detected both by HPLC (eluting slightly earlier than PTH-Gln) and by measurement of radioactivity (70 dpm $^3$H/pmol Cys).

Mass Spectrometry. Mass spectra was recorded on a tandem quadrupole Fourier transform mass spectrometer constructed at the University of Virginia. Operation of this instrument has been described previously, Hunt, D., et al., *Proc. Nat. Acad. Sci. USA*, Vol. 84, p. 620–23 (1987). Methodology for sequence analysis of peptides by laser photodissociation on the Fourier transform instrument has also been reported, Brinegar, A., et al., *Proc. Nat. Acad. Sci. USA*, Vol. 85, p. 3927–31 (1988).

Samples for mass analysis on the tandem quadrupole Fourier transform instrument were prepared by dissolving lyophilized HPLC fractions in 2–10 µl of 0.1% trifluoroacetic acid. A 0.5 to 1.0 µl aliquot of these solutions (10–50 pmol of peptide) was added to 1 µl of a 1/1 mixture of monothioglycerol/glycerol on a gold-plated, stainless-steel probe tip, 2 mm in diameter. Peptides were sputtered from this liquid matrix into the gas phase for mass analysis largely in the form of (M+H)$^+$ ions by bombarding the sample matrix with 6–10 keV Cs$^+$ ion projectiles. The latter ions were generated from a cesium ion gun (Antek, Palto, Calif.) mounted directly on the ion source of the spectrometer.

Methyl Ester Formation. A standard solution of 2 N HCl in methanol was prepared by adding 800 µl of acetyl chloride dropwise with stirring to 5 ml of methanol. After the solution had stood at room temperature for 5 min, 100 µl aliquots of the reagent were added to lyophilized HPLC fractions. Esterification was allowed to proceed for 2 hr at room temperature, and the solvent was then removed by lyophilization.

Results

Edman degradation of GDCF-2 yielded no sequence data, indicating that the N-terminus was blocked. Digestion with pyroglutaminase did not remove the blocking group but removed pyroglutamic acid from the control peptide. GDCF-2 was then digested with endopeptidases. Sequence analysis of the products of cleavage of carboxymethylated GDCF-2 with *Staphylococcus aureus* protease V8 or carboxymethylated, succinylated GDCF-2 with trypsin established the sequence of residues 19–76 (Table VI). The cleavage at Ser-21 by protease V8 was unusual; however, the same cleavage was observed in three separate digests. The sequence analysis data are presented in Table VII.

Peptides TS1 (1–19) and SP1 (1–21) both had blocked N-termini. SP1, containing the C-terminal sequence Arg-Lys-Ile-Ser, was analyzed by mass spectrometry. A mass spectrum recorded on 20 pmol of this material showed an abundant (M+H)$^+$ ion at m/z 2454.3. Conversion of the oligopeptide to the corresponding methyl ester shifted the observed (M+H)$^+$ ion to higher mass by 56 daltons, a result consistent with the addition of methyl groups (mass 14) to two carboxymethyl Cys residues, a free C-terminus, and one acidic residue in the peptide. Sub-digestion of SP1 fragment with endo-Asp-N afforded a single large peptide, the mass spectrum of which showed an abundant (M+H)$^+$ ion at m/z 2,246.2. Loss of 208 daltons in the above subdigestion can only be explained by placing the residues, pGluPro, in positions one and two of the parent molecule. Assignment of the third residue as Asp is dictated by the specificity of the enzyme employed in the cleavage reaction. An abundant fragment ion (m/z 2,131.3) resulting from the loss of these three N-terminal residues on the mass spectrum of the parent oligopeptide provided additional support for the above assignment.

Additional sequence information at the C-terminus of the endo-Asp-N cleavage product was obtained from fragmentation observed in the mass spectrum of the product generated as a result of on-probe acetylation. In this procedure the oligopeptide sample dissolved in the thioglycerol/glycerol matrix is treated with a 3/1 methanol/acetic anhydride for 30 s and then inserted back into the mass spectrometer. The resulting mass spectrum (M+H+=2331.4) contained abundant fragment ions of the type Y" at m/z 545, 659, 760, 907, 1021, and 1184 that allowed the C-terminal sequence to be extended back from the C-terminus by an additional five residues. This established the sequence of residues Tyr-13 to Ser-21.

Subdigestion of SP1 with both endo-Asp-N and chymotrypsin afforded a single large oligopeptide, the methyl ester of which afforded a mass spectrum containing an abundant ion at m/z 1342.1. This is the predicted mass of the (M+H)$^+$ ion for the peptide formed by cleavage of 8 residues from the C-terminus of the parent molecule. The complete mass spectrum of this oligopeptide is shown in FIG. 2. Fragment ions resulting from internal cleavage of the chain at Pro-8 appear at m/z 197, 298, 473, 648, and 843, and allow assignment of the sequence Pro-8 to Try-13. The last four of these ions suffer partial loss of water and thus appear as doublets separated by 18 mass units. Additional 18 mass unit doublets corresponding to fragment ions of type Y" (8) (m/z 896.6/914.6, 1010.7/1028.7, 1123.9/1141.9) allow placement of three additional residues, Ile-Asn-Ala on the N-terminal side of Pro-8. The first two residues in the peptide are assigned as Asp-Ala to account for the remaining mass of the molecule (200.1 daltons) and the expected specificity of the endo-Asp-N enzyme.

The N-terminal sequence obtained by tandem mass spectrometry was subsequently confirmed in part as follows. Cleavage of $^3$H-carboxymethylated GDCF-2 with endoproteinase Asp-N yielded a 51 residue peptide containing all the radioactivity. Edman degradation of this peptide, D1, yielded a sequence corresponding to the sequence of residues 3–23 (Table VII).

Discussion of Results

The complete amino acid sequence of GDCF-2 was determined by Edman degradation and tandem MS. Although the sequence of residues 19–76 was obtained with relative ease by fragmentation and Edman degradation, the sequence of the blocked N-terminal 18 residues posed a difficult problem. Pyroglutamic acid was suspected to be the N-terminal residue but digestion with pyroglutamate aminopeptidase did not deblock GDCF-2 (due to the presence of proline at position 2). Tandem MS provided the sequence of peptide SP1 (1–21) expending only picomole amounts of the peptide. In addition, partial sequence data for native GDCF-1 were obtained by this method. These data indicate that GDCF-2 and GDCF-1 are virtually identical molecules but that the N-terminus of GDCF-1 may contain an additional residue and/or a different N-terminal post-translational modification (data not shown). The four half-cystines of GDCF-1 were found to participate in two disulfide bridges, Cys-11 or Cys-12 to Cys-36 and Cys-11 or Cys-12 to Cys-52 (GDCF-2 numbering).

The molecular weight of GDCF-2, calculated from the amino acid sequence, is 8700 kDa whereas both native and carboxymethylated GDCF-2 migrate as 13 kDa species on NaDoDSO$_4$/PAGE gels. We have no explanation for this discrepancy since no post-translational modifications, other than the formation of pyroglutamic acid, were detected in the sequence analyses. A similar discrepancy between predicted and observed molecular weight was reported for the melanoma growth factor, MGSA, which consists of 73 amino acids, but migrates as a 13 kDa species, Richmond, A., et al, supra. Anomalous migrations on NaDoDSO$_4$/PAGE gels have been commonly observed for basic proteins, Tung et al., supra.

EXAMPLE IV

Cloning Of Monocyte-Chemoattractant Protein-1 (MCP-1) Full Length cDNA

In Example I above, we purified to homogeneity two human monocyte chemoattractants from the culture fluid of a glioma cell line. Although these two attractants could be separated into two peaks by action exchange HPLC, their amino acid compositions were identical. Likewise, two cation exchange HPLC peaks of monocyte chemotactic activity, purified from culture fluid of PHA-stimulated human blood lymphocytes in Example II, were indistinguishable in amino acid composition to one another and to the glioma-derived proteins. The complete amino acid sequence of one of the monocyte chemoattractants purified from glioma culture fluid was determined on a set of partial digests by a combination of Edman degradation and mass spectrometry in Example III. A single protein chain with a blocked N-terminus (pyroglutamic acid) and a total of 76 residues was identified (see Table VI), in the present example it is named Monocyte Chemoattractant Protein-1 (MCP-1). In the present example we provide for the cloning of MCP-1 full-length cDNA, its hybridization to genomic DNA from other species, and detection of MCP-1 mRNA in normal cells stimulated by mediators of inflammation.
Materials and Methods Restriction enzymes, DNA modifying enzymes, and reagents for cDNA preparation were from Bethesda Research Laboratories, Bethesda, Md. DNA sequencing reagents were from United States Biochemicals. Radiochemicals were from Amersham Corp. or New England Nuclear. Lambda ZAP II vector was from Stratagene (La Jolla, Calif.). Cytokines were from Boehringer Mannheim.

Total RNA was isolated from glioma cell line U-105MG by the guanidinium-isothiocynate method; and poly(A) RNA was isolated by oligo(dt)-cellulose chromatography, T. Maniatis, et al., "Molecular Cloning: A Laboratory Manual" (Cold Spring Harbor Lab., Cold Spring Harbor, N.Y. (1982)) herein incorporated by reference. cDNA was synthesized by a modification of the Gubler and Hoffman method [Gene, vol. 25, p. 263–269 (1983) herein incorporated by reference) and was used to prepare a library in LAMBDA ZAP II® vector by the method of J. M. Short, et al., *Nucleic Acids Res.*, vol. 16, pp. 7583–7600 (1988), herein incorporated by reference. Oligodeoxynucleotides were synthesized by the phosphoramidite method of S. P. Adams, et al., *J. Am. Chem. Soc.*, vol. 105, pp. 661–663 (1983) herein incorporated by reference, and purified by HPLC. Probes (FIG. 1B) were synthesized on the basis of the sequence of a peptide fragment (SP-4, FIG. 1A) generated by digestion of MCP-1 with *S. aureus* V8 protease. Approximately 5×10 recombinant phage from the cDNA library were screened by high-density plaque hybridization (by a utilization of the methods of T. Maniatis, et al., supra, and W. D. Benton, et al., Science vol. 196, pp. 180–182 (1977) herein incorporated by reference] with a mixture of $^{32}$P-labeled oligonucleotides SP-4-A and SP-4-B (FIG. 1B). Hybridization to nitrocellulose filters was carried out overnight at 45° C. in a solution containing 6×standard saline citrate (SSC), 5× Denhardt's solution, 0.05% sodium pyrophosphate, 1% NaDodSO$_4$, 100 µg/ml heat-denatured, sheared, salmon sperm DNA and 1×10$^6$ dpm/ml probe. Filters were washed once with 6×SSC, 0.1% NaDodSO$_4$ at 45° C. for 5 min, three times at 35° C. for 30 min, and were dried and exposed overnight to XS-5 film (Kodak) with an intensifying screen at −80° C. Phagemids carried within LAMBDA ZAP II® recombinants were rescued with helper phage by the method of J. M. Short, et al., supra. cDNA inserts were subcloned into M13 mp19 by the method of C. Yanisch-Perron, et al., herein incorporated by reference, and single strands were sequenced on field gradient gels [such as those provided by W. Ansorge, et al., *J. Biochem. Biophys. Meth.*, vol. 10, pp. 237–243 (1984) herein incorporated by reference] by the dideoxynucleoside triphosphate chain termination method of F. Sanger, et al., *Proc. Nat. Acad. Sci. U.S.A.*, vol. 74, pp. 5463–5467 (1977) herein incorporated by reference. Sequence data were compiled and analyzed with computer assistance by a method similar to that of C. Queen, et al., *Nucleic Acids Res.*, vol. 12, pp. 581–599, herein incorporated by reference.

Human PBMNL's were stimulated with 2.5 µg/ml of PHA, 10 µg/ml LPS, or 100 units/ml of the following human recombinant LPS-free cytokines: IL-Lβ, IL-2, TNFα, IFN-lambda. Northern blot analysis of poly(A) RNA was done by the glyoxaldimethylsulfoxide method [T. Maniatis, et al., supra] in a 1% agarose gel with a probe of MCP-1 cDNA insert labeled with [α-$^{32}$]CTP by random priming similar to the method of A. P. Feinburg, et al., *Anal. Biochem.*, vol. 132, pp. 6–13 (1983) herein incorporated by reference. Filters were hybridized at 42° C. overnight in 50% formamide, 1 M NaCl, 5× Denhardt's solution, 1 mM EDTA, 0.1% sarkosyl, 100 µg/ml sheared-denatured salmon sperm DNA, 1×10$^6$ dpm/ml probe and 50 mM piperazine-N,N'-bis [2-ethanesulfonic acid], pH 7. Filters were washed twice with 2×SSC, 0.1% NaDodSO$_4$ at 37° C. for 30 min and 0.1×SSC, 0.1% NaDodSO$_4$ at 50° C. for 30 min prior to autoradiographic exposure.

Southern blot analysis was performed as described by T. Maniatis, et al., supra, in a 1% agarose gel with 10 µg restriction-enzyme-cleaved DNA per lane. Hybridization was as described for library screening except that transfers were made to nylon filters, hybridization temperature was 65° C. and the probe was $^{32}$P-labeled MCP-1 cDNA. Filters were washed once in the hybridization solution used for library screening at 65° C. for 1 hr, then twice in 0.1×SSC, 0.1% NaDodSO$_4$ at 48° C. for 30 min.

RESULTS

A cDNA library was constructed with poly (A) RNA from the human glioma cell line (U-105MG) in cloning vector LAMBDA ZAP II. Approximately 5×10$^5$ recombinant phage were screened with the oligonucleotide probes shown in FIG. 1B. Forty-eight positive signals on duplicate filters were obtained (~0.01% abundance). Fifteen clones were plaque purified and phagemid DNA was prepared. By preliminary nucleotide sequence analysis, at least three clones coded for MCP-1. The insert from the clone with the longest 5' untranslated region was sequenced (FIGS. 1C and 2).

Based on the amino acid sequence of pure MCP-1 as determined in Example III, the mature form of the protein starts with glutamine at residue 24 (nucleotide 70) (see FIG. 2). The amino acid sequence deduced from nucleotides 70 to 297 is identical to the directly determined 76 residue sequence of pure MCP-1. The cDNA sequence contains an in-frame methionine triplet 69 nucleotides upstream from the triplet corresponding to the $NH_2$-terminus of MCP-1. Seven of the 9 residues in the methionine triplet region, CCAGCATGA, match the sequence reported by M. Kozak, Cell, vol. 44, pp. 283–292 (1986) to be optimal for translation initiation. The length and hydrophobic character of the deduced amino acid sequence from the methionine to the $NH_2$-terminus of MCP-1 are typical of a signal peptide according to the teachings of G. von Heijne, Eur. J. Biochem., vol. 133, pp. 17–21 (1983). There is a single consensus sequence for N-linked glycosylation targeting amino acid 38.

The A+T content of the 3' untranslated region (66%) is not nearly as high as that found in some transiently expressed mRNA's, G. Shaw, et al., Cell, vol. 46, pp. 659–667 (1986). Unlike a number of genes encoding proteins related to the inflammatory response [D. Caput, et al., Proc. Natl. Acad. Sci. U.S.A., vol. 83, pp. 1670–1674 (1986)], there is no 8-nucleotide sequence, TTATTTAT, in the 3' untranslated region.

Figure 3:
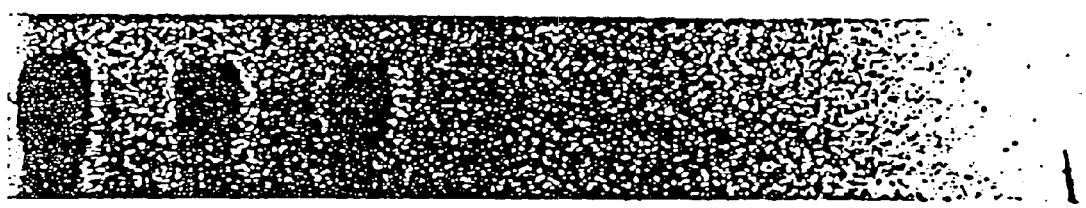
FIG. 3. Expression of MCP-1 mRNA in tumor cell lines. Five micrograms of poly(A) mRNA from each cell line were used. The first 5 blots are from glioma lines. SK-RC29, UMRC 2: renal cell carcinomas. HOS: osteosarcoma. GCT: fibrous histiocytoma. HL60, U937, Raji, Jurkat, H9: leukemia or lymphoma cell lines.

In a survey of 5 different glioma cell lines, it was reported that all released chemotactic activity for human monocytes [Kuratsu, et al., J. Natl. Cancer Inst., vol. 81, pp. 347–351: (1989), incorporated herein by reference]. It was therefore of interest to probe these and other tumor cell lines for MCP-1 mRNA message. FIG. 3 shows Northern blots with a cDNA probe for MCP-1. The high and low mRNA, respectively, of gliomas U-105MG and KMG-5 correlates with observed levels of chemotactic activity produced by these two lines as reported by Kuratsu, et al., supra. MCP-1 mRNA was not detected in other human tumor cell lines.

Figure 4A:
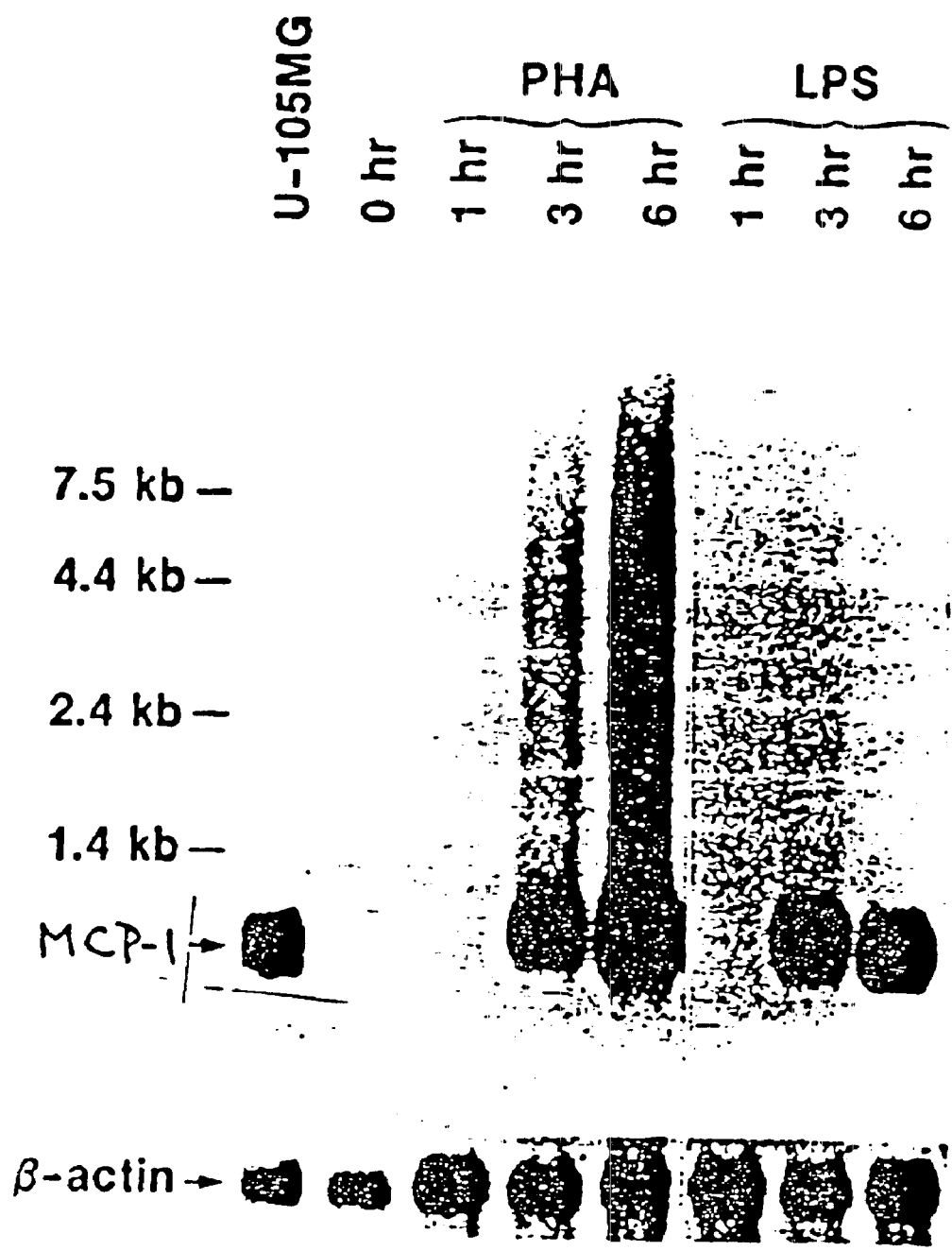
FIGS. 4A–4B. Induction of MCP-1 mRNA in human PBMNL's by mitogens or human recombinant cytokines. A. PBMNL's were cultured with 2.5 µg/ml PHA or 10 µg/ml LPS, and mRNA was extracted at the indicated times. B. Cells were cultured with 100 U/ml of each cytokine for 6 hours; then mRNA was extracted.
Figure 4B:
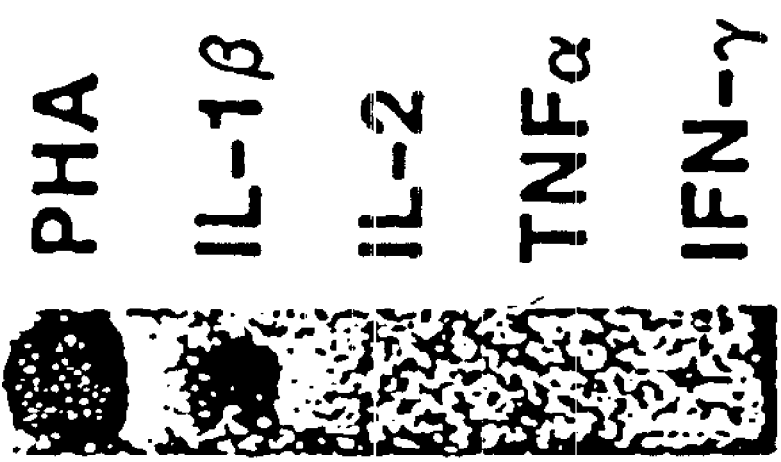

Since PBMNL-derived MCP-1 was indistinguishable from glioma-derived MCP-1, we did Northern blot analyses of mRNA from PBMNL's stimulated with PHA. No mRNA was detected before stimulation, but high levels of mRNA were detected 3 and 6 hours after addition of PHA (FIG. 4A). Ten µg/ml of LPS also induced high mRNA levels in these cells. IL-LB induced MCP-1 mRNA, though the level was less than for PHA (FIG. 4B). Induction of MCP-1 mRNA by IL-2, TNFα, or IFN-lambda was not detected.

Figure 5:
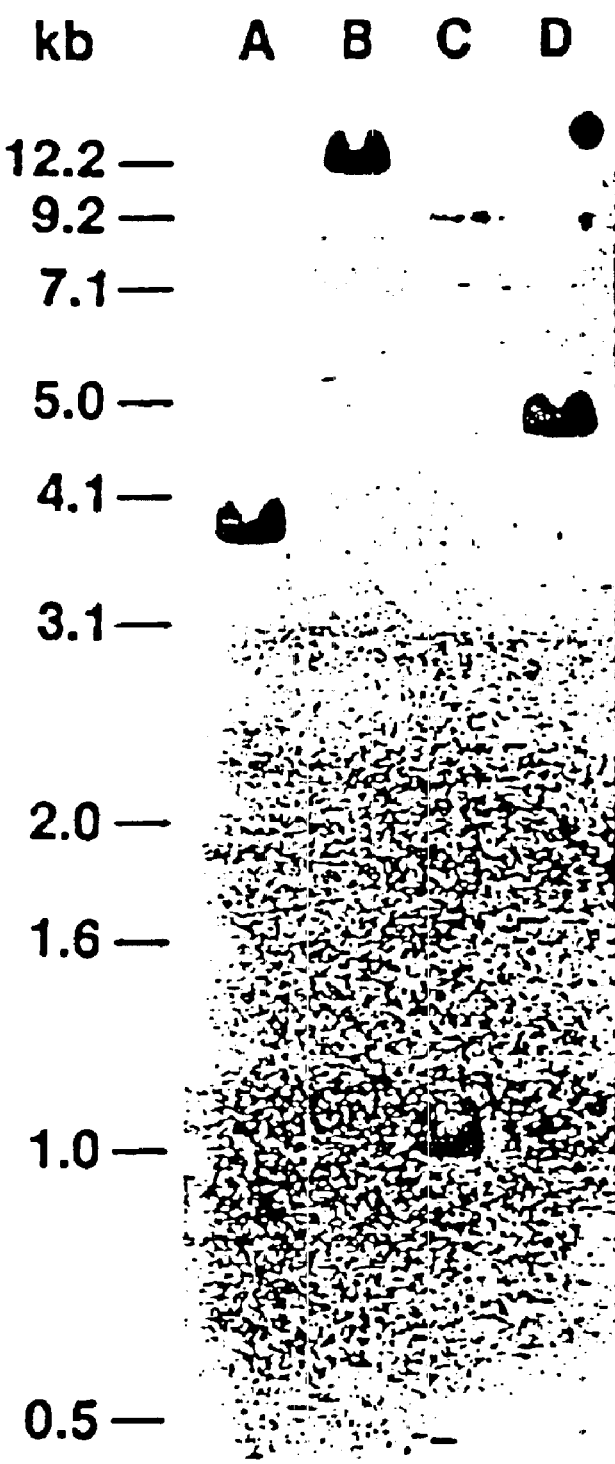
FIG. 5. Southern blotting analysis of human genomic DNA digested with various endonucleases. A. EcoRI. B. BamHI. C. PstI. D. HindIII.
Figure 6:
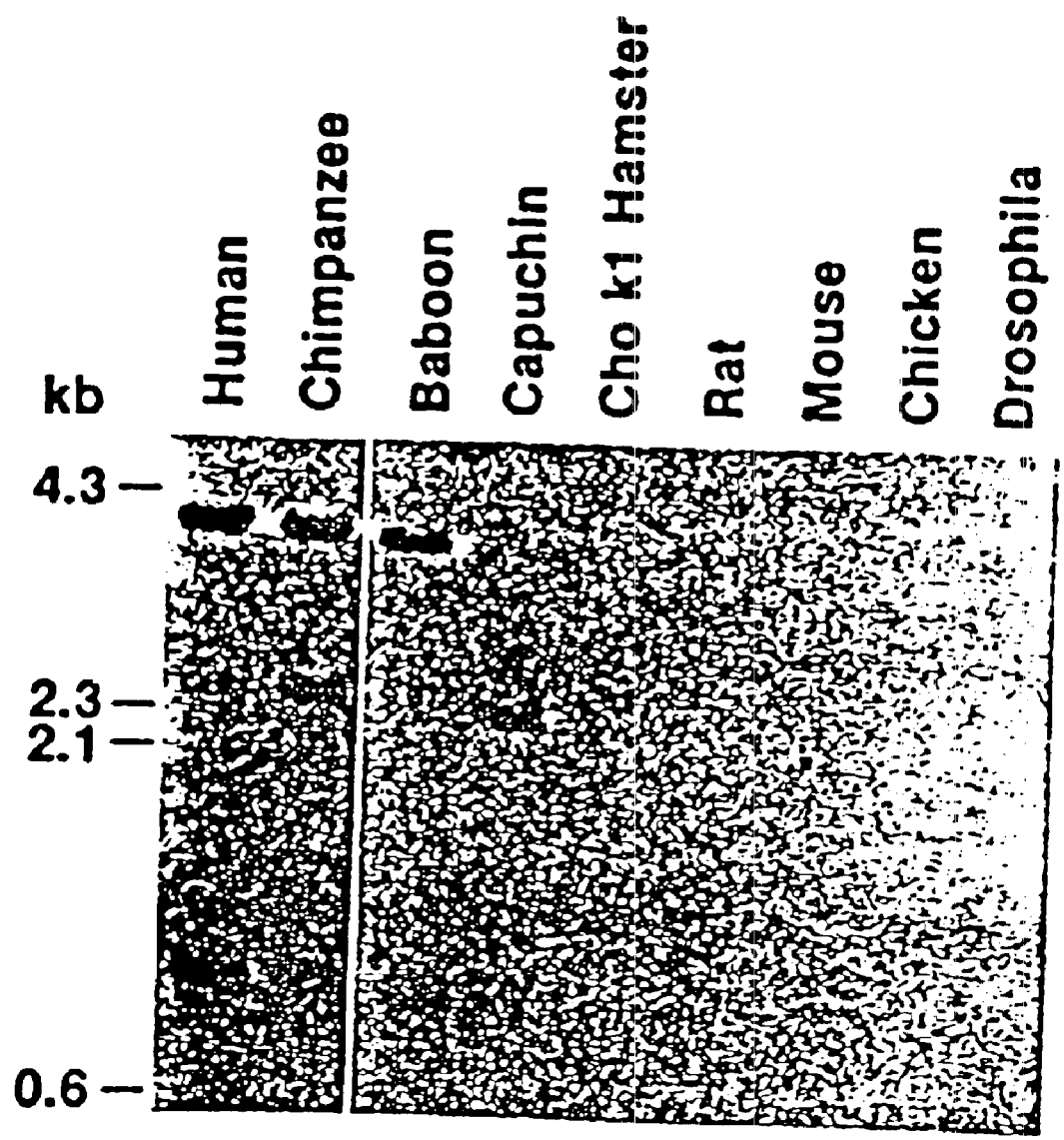
FIG. 6. Hybridization of MCP-1 cDNA with genomic DNA from various species.

To identify genomic DNA fragments carrying the gene for MCP-1, human DNA restriction endonuclease digests were analyzed by Southern blot (FIG. 5). After BamHI or HindIII digestion, a single band was seen. PstI digestion gave 2 major bands, which is in agreement with the fact there is a PstI restriction site in the MCP-1 cDNA. The data show that there is a single MCP-1 gene. DNA from different species was digested with EcoRI and hybridized to the same probe (FIG. 6). Under conditions of high stringency, hybridization occurred with DNA of chimpanzee, baboon and capuchin, but not of other species.

Discussion

In view of the fact that MCP-1's from glioma cells and mitogen-stimulated PBMNL's are indistinguishable, either glioma cells or stimulated PBMNL's can provide mRNA for cDNA library construction. We selected the glioma cell line, since it produced the attractant constitutively. The cDNA clone derived from the glioma cell library detected mRNA in both glioma cells and PHA-stimulated PBMNL's. This is consistent with our observation that the amino acid compositions of MCP-1's from the two sources are identical.

Although MCP-1 mRNA was detected in several glioma cell lines, no message mRNA was found in 9 cell lines representing other types of tumors. Thus, expression of the MCP-1 gene is not a property of all neoplastic cells.

The amino acid composition of a monocyte chemoattractant produced by aortic smooth muscle cells of the baboon [A. J. Valente, et al., Biochemistry, vol. 27, pp. 4162–4168 (1988), herein incorporated by reference] is identical to that of MCP-1 as determined in Example III herein. Hybridization of the MCP-1 cDNA probe with baboon DNA (FIG. 6) is added evidence for the relationship between MCP-1 and the smooth muscle product, and indicates that both lymphocytes and vascular smooth muscle cells can produce this attractant.

EXAMPLE V

Treatment of Infection in a Human

When an effective, infection treating amount of one of the purified peptide products, prepared in either Examples I or II above, or MCP-1 synthesized by methods provided herein, is administered to a human, and to the site of an infected area in a human, control of that infection is expected. The volume of the infection treating peptide composition to be administered, and the frequency of administration will be determined by the treating physician.

EXAMPLE VI

Treatment of a Neoplasm in a Human

When an effective, neoplastic treating amount of one of the purified peptide products, prepared in either Examples I or II above, or MCP-1 synthesized by methods provided herein, is administered to a human, and to the site of a neoplasm in a human, control of the neoplasm is expected due to peptide induced accumulation of monocytes at the site. The volume of the neoplasm-treating peptide composition to be administered, and the frequency of administration will be determined by the treating physician.

EXAMPLE VII

Treatment of Inflammatory Disease with a Peptide Inhibitor

Since the structure of the GDCF-2 peptide provided herein is now known, as well as MCP-1, it is possible to synthesize short peptides reflecting partial sequences of the complete GDCF-2 peptide or MCP-1 protein. These synthesized peptides can be screened to find one that binds to the monocyte receptor site without stimulating a chemotactic response. If such a peptide is found, it can be used in clinical trials to control symptoms in human chronic inflammatory diseases that are characterized by inappropriate monocyte infiltration. The volume of the infection-treating peptide composition to be administered, and the frequency of administration will be determined by the treating physician.

TABLE I

Purification of Human GDCF

| | Total protein, mg | Total MCA, units[3] | Specific activity units/mg |
|---|---|---|---|
| Crude supernatant | 29[1] | 200,000 | 6,900 |
| Concentrated and dialyzed supernatant | 29[1] | 190,000 | 6,600 |
| Orange-A Sepharose | 0.52[1] | 148,000 | 288,000 |
| CM-HPLC | | | |
| P-I (frs 36 + 37) | 0.03[1] | 21,600 | 720,000 |
| P-II (frs 45 + 46) | 0.03[1] | 18,200 | 607,000 |
| Reverse phase HPLC | | | |
| GDCF-1 | 0.005[2] | 5,700 | 1,140,000 |
| GDCF-2 | 0.019[2] | 20,000 | 1,053,000 |

[1]Protein concentration was determined by dye protein assay with bovine serum albumin as standard.
[2]Protein concentration was calculated from amino acid composition.
[3]MCA concentration of 1 unit/ml was defined as the reciprocal of the dilution at which 50% of the maximal chemotactic response was obtained.

TABLE II

Amino Acid Composition of Human GDCF

| | Residues per molecule[1] | |
|---|---|---|
| Amino Acid | GDCF-1 | GDCF-2[2] |
| Asp + Asn | 7.6 | 8.0 |
| Thr | 6.8 | 6.8 |
| Ser | 4.6 | 4.6 |
| Glu + Gln | 8.4 | 8.0 |
| Pro | 5.1 | 4.5 |
| Gly | 2.0 | 0.3 |
| Ala | 5.7 | 6.1 |
| Val | 4.7 | 4.5 |
| Met | 0.9 | 0.7 |
| Ile | 5.3 | 5.0 |
| Leu | 2.3 | 2.3 |
| Tyr | 1.8 | 1.8 |
| Phe | 2.1 | 2.0 |
| His | 1.2 | 0.9 |
| Lys | 8.6 | 9.1 |
| Arg | 4.0 | 3.6 |
| Cys | ND[3] | 3.5[4] |
| Trp | ND | ND |

[1]The data were calculated on the basis of a total of 74 residual/molecule.
[2]GDCF-2 was reduced and $^3$H-carboxymethylated for composition analysis.
[3]ND: not determined.
[4]H-carboxymethylcysteine.

TABLE III

Assay to distinguish chemotactic from chemokinetic activity in Glioma Cell Line U-105MG Derived Purified Peptide Products

| Concentration in top wells (M) | Concentration in bottom wells (M) | | | |
|---|---|---|---|---|
| | 0 | $4 \times 10^{-11}$ | $2 \times 10^{-10}$ | $10^{-9}$ |
| | Monocyte migration, % of input cell number ± SEM | | | |
| A: GDCF-1 | | | | |
| 0 | 1 ± 0.2 | 5 ± 0.9 | 22 ± 2.4 | 35 ± 0.7 |
| $4 \times 10^{-11}$ | 1 ± 0.2 | 4 ± 0.5 | 15 ± 1.3 | 34 ± 4.6 |
| $2 \times 10^{-10}$ | 2 ± 0.4 | 2 ± 0.3 | 3 ± 1.2 | 21 ± 4.2 |
| $10^{-9}$ | 1 ± 0.2 | 1 ± 0.1 | 1 ± 0.1 | 3 ± 0.2 |
| B: GDCF-2 | | | | |
| 0 | 2 ± 0.2 | 12 ± 1.8 | 25 ± 6.2 | 27 ± 3.9 |
| $4 \times 10^{-11}$ | 1 ± 0.1 | 5 ± 0.5 | 18 ± 0.6 | 26 ± 5.0 |
| $2 \times 10^{-10}$ | 3 ± 0.5 | 2 ± 0.2 | 5 ± 0.6 | 24 ± 1.5 |
| $10^{-9}$ | 1 ± 0.1 | 2 ± 0.1 | 2 ± 0.1 | 4 ± 0.1 |

TABLE IV

Amino Acid Composition of Human LDCF-1 and -2

| | Residues per molecule | |
|---|---|---|
| Amino Acid | LDCF-1 | LDCF-2 |
| Asp + Asn | 8.1 | 7.8 |
| Thr | 6.4 | 6.7 |
| Ser | 5.6 | 4.7 |
| Glu + Gln | 9.4 | 8.9 |
| Pro | 5.4 | 5.2 |
| Gly | 2.2 | 3.2 |
| Ala | 6.2 | 6.0 |
| Val | 4.8 | 4.9 |
| Met | 0.7 | 0.9 |
| Ile | 4.8 | 5.2 |
| Leu | 2.4 | 2.3 |
| Tyr | 1.6 | 1.5 |
| Phe | 1.9 | 2.1 |
| His | 1.2 | 1.2 |
| Lys | 8.0 | 8.4 |
| Arg | 3.7 | 3.7 |
| Cys | ND[a] | ND |
| Trp | ND | ND |

[a]ND: not determined.

TABLE V

Purification of Monocyte Chemotactic Peptides

| | Total protein, mg | Total MCA units[c] | Specific activity units/mg |
|---|---|---|---|
| Crude supernatant | 79[a] | 300,000 | 3,800 |
| Concentrated and dialyzed supernatant | 57[a] | 162,000 | 2,800 |
| Orange-A Sepharose | | | |
| Pass-through | 55[a] | 89,000 | 1,600 |
| Bound | 1.7[a] | 106,000 | 62,000 |
| CM-HPLC | | | |
| P-I | 0.10[a] | 30,000 | 300,000 |
| P-II | 0.28[a] | 16,000 | 57,000 |
| RP-HPLC | | | |
| LDCF-1 | 0.042[b] | 20,000 | 480,000 |
| LDCF-2 | 0.020[b] | 10,000 | 500,000 |

[a]Protein concentration was determined by dye protein assay with bovine serum albumin as standard.
[b]Protein concentration was calculated from amino acid composition.
[c]Chemotactic activity of 1 unit/ml was defined as the reciprocal of the dilution at which 50% of the maximal chemotactic response was obtained.

TABLE VI

Amino Acid Sequence for GDCF-2

Amino acid sequence of GDCF-2 deduced from S. aureus protease V8 (SP) and aspartylendopeptidase P. fragi protease (D) peptides and from tryptic peptides of succinylated GDCF-2 (TS). _____, tandem MS; _____, Edman degradation; ------, unsequenced portions of a particular peptide.

```
1         10        20        30
XPDAINAPVTCCYNFTNRKISVQRLASYRRITSSKCPKE 40        50        60        70
AVIFKTIVAKEICADPKQKWVQDSMDHLDKQTQTPKT
-----SP3---------------SP4-----------
-------------TS4---------------------
-------------
``` where:
- A is alanine;
- C is cysteine;
- D is aspartic acid;
- E is glutamic acid;
- F is phenylalanine;
- H is histidine;
- I is isoleucine;
- K is lysine;
- L is leucine;
- M is methionine;
- N is asparagine;
- P is proline;
- Q is glutamine;
- R is arginine;
- S is serine;
- T is threonine;
- V is valine;
- W is tryptophan;
- X is tryrosine; and
- Y is pyroglutamic acid.

TABLE VII

| | Peptide PTH Amino Acid (yield)+ | | | | | | |
|---|---|---|---|---|---|---|---|
| Cycle | D1 | SP2 | SP3 | SP4 | TS2 | TS3 | TS4 |
| 1 | D (27) | V (72) | A (1494) | I (191) | K (320) | L (60) | I (279) |
| 2 | A (26) | Q (84) | V (582) | C (185) | I (281) | A (124) | T (110) |
| 3 | I (24) | R (23) | I (490) | A (168) | S (173) | S (102) | S (124) |
| 4 | N (21) | L (60) | F (463) | D (123) | V (200) | Y (78) | S (158) |
| 5 | A (23) | A (72) | K (447) | P (131) | Q (130) | R (27) | K (76) |
| 6 | P (24) | S (61) | T (228) | K (93) | R (68) | R (12) | C (62) |
| 7 | V (11) | Y (41) | I (329) | Q (101) | | | P (53) |
| 8 | T (10) | R (34) | V (300) | K (81) | | | K (64) |
| 9 | C (11) | R (37) | A (321) | W (30) | | | E (53) |
| 10 | C (12) | I (42) | K (285) | V (59) | | | A (42) |
| 11 | Y (12) | T (34) | E (143) | Q (74) | | | V (30) |
| 12 | N (12) | S (28) | | D (56) | | | I (34) |
| 13 | F (16) | S (27) | | S (37) | | | F (29) |
| 14 | T (6) | K (11) | | M (33) | | | K (29) |
| 15 | N (8) | C (22) | | H (18) | | | T (18) |
| 16 | R (6) | P (19) | | L (31) | | | I (17) |
| 17 | K (2) | K (7) | | D (23) | | | V (15) |
| 18 | I (9) | E (5) | | K (17) | | | A (20) |
| 19 | S (3) | | | Q (27) | | | K (16) |
| 20 | V (3) | | | T (14) | | | E (10) |
| 21 | Q (8) | | | Q (19) | | | I (10) |
| 22 | — | | | T (11) | | | C (13) |
| 23 | L (6) | | | P (8) | | | A (11) |
| 24 | | | | K (5) | | | D (7) |
| 25 | | | | T (5) | | | P (7) |
| 26 | | | | | | | K (4) |
| 27 | | | | | | | Q (4) |
| 28 | | | | | | | K (1) |
| 29 | | | | | | | W (2) |
| 30 | | | | | | | V (2) |
| 31 | | | | | | | Q (2) |
| 32 | | | | | | | D (4) |
| 33 | | | | | | | S (1) |

TABLE VII-continued

| | | | Peptide PTH Amino Acid (yield)+ | | | | |
|---|---|---|---|---|---|---|---|
| Cycle | D1 | SP2 | SP3 | SP4 | TS2 | TS3 | TS4 |
| 34 | | | | | | | M (1) |
| 35 | | | | | | | — |
| 36 | | | | | | | H (2) |
| 37 | | | | | | | L (1) |

+The yield at each cycle is in pmoles. C = carboxymethylcysteine, K = succinylated lysine.

Pharmaceutical Compositions

The purified peptide products of the present invention, as well as MCP-1 or synthesized MCP encompassed by the present invention, may be made into pharmaceutical compositions by combination with appropriate pharmaceutically acceptable carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective route of administration. The following methods of administration and excipients provided therewith, are merely exemplary of available methods which may be employed to deliver the purified peptide products of the present invention to the site of an antigen challenge, or a neoplasm in a human, and they should in no way be construed as limiting the present invention.

In pharmaceutical dosage forms, the monocyte chemotactic compounds of the present invention may be used along or in appropriate association, as well as in combination with other pharmaceutically active compounds.

In the case of oral preparations, the purified peptide products of the present invention, as well as MCP-1 or MCP, may be used alone or in combination with appropriate additives to make tablets, powders, granules or capsules, e.g., with conventional additives such as lactose, mannitol, corn starch or potato starch; with binders such as crystalline cellulose, cellulose derivatives, acacia, corn starch, potato starch or sodium carboxymethyl-cellulose; with lubricants such as talc or magnesium stearate; and if desired, with diluents, buffering agents, moistening agents, preservatives and flavoring agents.

Furthermore, the peptide products of the present invention, as well as MCP or MCP-1, may be made into suppositories by mixing with a variety of bases such as emulsifying bases or water-soluble bases.

The purified peptide products of the present invention, as well as MCP or MCP-1, may be formulated into preparations for injections by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the cases of inhalations or aerosol preparations, the purified peptide products of the present invention, as well as MCP or MCP-1, may be in the form of a liquid or minute powder in an aerosol container with gas or liquid spraying agents, and if desired, together with conventional adjuvants such as humidifying agents. They may also be formulated as pharmaceuticals for non-pressurized preparations such as in a nebulizer or an atomizer.

The amount of the purified peptide products of the present invention, as well as MCP or MCP-1 encompassed by the present invention, to be used varies according to the degree of infection or the size and type of neoplasm encountered in a human. A suitable dosage is envisioned at about 0.001–1.0 mg/kg body weight per day for treatment of infection or neoplasms in a human. The preferred dosage being that amount sufficient to effectively treat an infection or neoplasm in a human.

A method of treatment utilizing the purified peptide products of the present invention, as well as MCP or MCP-1 encompassed by the present invention, can also be had by oral ingestion of one of the peptides of the present invention with a pharmaceutically acceptable carrier.

Unit dosage forms for oral administration such as syrups, elixirs, and suspensions wherein each dosage unit, e.g., teaspoonful, tablespoonful, contains a predetermined amount of the purified peptide product of the present invention or MCP or MCP-1. Inclusion of pharmaceutically acceptable excipients, are readily known by those skilled in the art.

Parenteral administration of the purified peptide products of the present invention, as well as MCP or MCP-1, can be had by administration with a pharmaceutically acceptable carrier, such as Sterile Water for Injection, USP, or by normal saline.

The purified peptide products of the present invention, as well as MCP or MCP-1, can be administered rectally via a suppository. The suppository can include vehicles such as cocoa butter, carbowaxes and polyethylene glycols, which melt at body temperature, yet are solidified at room temperature.

The purified peptide products of the present invention, as well as MCP or MCP-1, can be utilized in aerosol formulation to be administered via inhalation. The purified peptide products can be formulated into pressurized aerosol containers together with pharmaceutically acceptable propellants, such as dichlorodifluoro-methane, propane, nitrogen and the like.

It is also recognized that a skilled practitioner in the art may desire to modify the above modes of administration, in order to more effectively deliver one of the purified peptide products, as well as MCP or MCP-1, directly to the site of an infection or neoplasm in a human body. Such modification and direct administration of one of the purified peptides of the present invention, MCP or MCP-1, is fully comprehended herein, and encompassed by the present invention.

Furthermore, it is envisioned that an injectable pharmacological composition of the peptide products of the present invention, as well as MCP or MCP-1, to be administered directly to the site of an infection or neoplasm, would contain a concentration of the peptide(s), encompassed herein, that is anticipated to cause monocyte accumulation at locally injected tissue sites of human patients. This concentration is thought to be preferably not less than $10^{-8}$M and not more than $10^{-6}$M.

Lastly, it is to be understood that the present invention is only limited by the scope of the appended claims.

What is claimed is:

1. A pure peptide product derived from human glioma cells exhibiting monocyte chemotactic activity at a concentration of 1 nM; said peptide product exhibiting an estimated molecular mass of about 8,400 daltons.

2. The pure peptide product of claim 1 obtained by the process comprising the steps of:

(I) culturing live cells derived from:
   (a) human glioma cell line U-105MG, or
   (b) human peripheral blood mononuclear leukocytes, in an appropriate growth medium (II) separating said cells from said growth medium;

(III) chromatographing said growth medium on an Orange-A Sepharose column, utilizing an appropriate solvent, and collecting the fractions which contain the desired peptides;

(IV) chromatographing said peptide containing fraction obtained in Step IV on an appropriate cation-exchange HPLC column, utilizing appropriate solvents, and collecting the fractions which contain said desired peptides;

(V) chromatographing said peptide containing fractions obtained in Step 1V on a reverse phase HPLC column, utilizing an appropriate solvent, and collecting the fractions containing said desired peptides; and (VI) removing liquid from said peptide containing fractions obtained in Step V, to give said peptide product as in a solid form.

3. The pure peptide product of claim 1, which is derived from glioma cell line U-105MG, said peptide product comprising an amino acid sequence of:

```
1         10         20         30
XPDAINAPVTCCYNFTNRKISVQRLASYRRITSSKCPKE 40        50         60         70
AVIFKTIVAKEICADPKQKWVQDSMDHLDKQTQTPKT
``` wherein:
A is Alanine;
C is Cysteine;
D is Aspartic Acid;
E is Glutamic Acid;
F is Phenylalanine;
H is Histidine;
I is Isoleucine;
K is Lysine;
L is Leucine;
M is Methionine;
N is Asparagine;
P is Proline;
Q is Glutamine;
R is Arginine;
S is Serine;
T is Threonine;
V is Valine;
W is Tryptophan;
Y is Tryrosine; and
X is pyroglutamic acid.

4. A pure peptide product exhibiting optimal monocyte chemotactic activity at a concentration of 1 nM said peptide product exhibiting an estimated molecular mass of about 8,400 daltons and comprising an amino acid sequence of:

```
1         10         20         30
XPDAINAPVTCCYNFTNRKISVQRLASYRRITSSKCPKE 40        50         60         70
AVLFKTTYAKEICADPKQKWVQDSMDHLDKQTQTPKT
``` wherein:
A is Alanine;
C is Cysteine;
D is Aspartic Acid;
E is Glutamic Acid;
F is Phenylalanine;
H is Histidine;
I is Isoleucine;
K is Lysine;
L is Leucine;
M is Methionine;
N is Asparagine;
P is Proline;
Q is Glutamine;
R is Arginine;
S is Serine;
T is Threonine;
V is Valine;
W is Tryptophan;
Y is Tryrosine; and
X is Pyroglutamic acid;
or conservative amino acid substitutions thereof.

or conservative amino acid substitutions thereof.

5. A recombinant peptide comprising the amino acid sequence:

```
1         10         20         30
QPDAINAPVTCCYNFTNRKISVQRLASYRRITSSKCPKE 40        50         60         70
AVIFKTIVAKEICADPKQKWVQDSMDHLDKQTQTPKT
``` wherein:
A is Alanine;
C is Cysteine;
D is Aspartic Acid;
E is Glutamic Acid;
F is Phenylalanine;
H is Histidine;
I is Isoleucine;
K is Lysine;
L is Leucine;
M is Methionine;
N is Asparagine;
P is Proline;
Q is Glutamine;
R is Arginine;
S is Serine;
T is Threonine;
V is Valine;
W is Tryptophan; and
Y is Tryrosine;

or conservative amino acid substitutions thereof.

6. An isolated peptide comprising an no acid sequence encoded by a nucleic acid sequence having a sequence of:
CAG CCA GAT GCA ATC AAT GCC CCA GTC ACC TGC
TGT TAT AAC TTC ACC AAT AGG AAG ATC TCA GTG
CAG AGG CTC GCG AGC TAT AGA AGA ATC ACC
AGC AGC AAG TGT CCC AAA GAA GCT GTG ATC
TTC AAG ACC ATT GTG GCC AAG GAG ATC TGT GCT
GAC CCC AAG CAG AAG TGG GTT CAG GAT TCC
ATG GAC CAC CTG GAC AAG CAA ACC CAA ACT
CCG AAG ACT.

7. An isolated peptide obtained by a process comprising the steps of:

(I) culturing a host cell transformed with a nucleic acid encoding a polypeptide comprising the amino acid sequence:

```
1         10        20        30
QPDAINAPVTCCYNFTNRKISVQRLASYRRITSSKCPKE 40        50        60        70
AVIFKTIVAKEICADPKQKWVQDSMDHLDKQTQTPKT
``` wherein:
A is Alanine;
C is Cysteine;
D is Aspartic Acid;
E is Glutamic Acid;
F is Phenylalanine;
H is Histidine;
I is Isoleucine;
K is Lysine;
L is Leucine;
M is Methionine;
N is Asparagine;
P is Proline;
Q is Glutamine;
R is Arginine;
S is Serine;
T is Threonine;
V is Valine;
W is Tryptophan; and
Y is Tryrosine;

or conservative amino acid substitutions thereof, (II) recovering the polypeptide from the cell.

8. A pharmaceutical composition comprising:

the pure peptide product of claim 1; and a pharmaceutically acceptable carrier therefor.

9. A pharmaceutical composition comprising:

the peptide of any of claims 5–7; and a pharmaceutically acceptable carrier therefor.

10. A method of preparing a pure peptide product, having a molecular weight of about 8,400 daltons, and exhibiting optimal monocyte chemotactic activity at a concentration of 1 nM; said method comprising the steps of:

(I) culturing live cells derived from:
 (a) human glioma cell line U-105MG, or
 (b) human peripheral blood mononuclear leukocytes, in an appropriate growth medium;

(II) separating said cells from said growth medium;

(III) chromatographing said growth medium on an Orange-A Sepharose column, utilizing an appropriate solvent, and collecting the factions which contain the desired peptides;

(IV) chromatographing said peptide containing fractions obtained in Step III on an appropriate cation change HPLC column, utilizing appropriate solvents, and collecting the fractions which contain said desired peptides;

(V) chromatographing said peptide containing faction obtained in Step IV on a reverse phase HPLC column, utilizing an appropriate solvent, and collecting the fractions containing said desired peptides; and (VI) removing liquids from said peptide containing fractions obtained in Step V, to give said peptide product in a solid form.

11. A method of treating neoplasms in a human which comprises administering to a human an effective neoplasm treating amount of the purified peptide product of claim 1.

12. A method of treating neoplasms in a human which comprises administering to a human an effective amount of the peptide of any of claims 5–7.

\* \* \* \* \*

UNITED STATES PATENT AND TRADEMARK OFFICE
CERTIFICATE OF CORRECTION

PATENT NO. : 6,869,924 B1
APPLICATION NO. : 07/330446
DATED : March 22, 2005
INVENTOR(S) : Yoshimura et al.

It is certified that error appears in the above-identified patent and that said Letters Patent is hereby corrected as shown below:

Front Page, (*) Notice, line 3: "by 1,826 days." should read --by 0 days.--

Col. 1, line 18: "thought in include" should read --thought to include--

Col. 2, line 32: "X is pyrolutamic acid." should read --X is pyroglutamic acid.--

Col. 4, line 33: ""The term "LAMBDA"" should read --The term "LAMBDA--

Col. 4, line 40: "Calif. 92037."" should read --Calif. 92037.--

Col. 4, line 47: "and extend of determined" should read --and extent of determined--

Col. 8, line 30: "include the B-lactamase" should read --include the β-lactamase"

Col. 9, line 17: "linear Nacl gradients" should read --linear NaCl gradients--

Col. 14, lines 31-32: "Line U-150MG Derived" should read --Line U-105MG Derived--

Col. 17, line 50: "Lambda ZAP II vector" should read --Lambda ZAP II® vector--

Col. 18, line 2: "Approximately 5x10" should read --Approximately 5x10$^5$--

Col. 18, line 34: "cytokines: IL-Lβ, IL-2," should read --cytokines: IL-1β, IL-2,--

Col. 18, line 62: "LAMBDA ZAP II." should read --LAMBDA ZAP II®.--

Col. 24, line 27: "X is tyrosine; and" should read --Y is tyrosine; and--

Col. 24, line 28: "Y is pyroglutamic acid." should read --X is pyroglutamic acid.--

UNITED STATES PATENT AND TRADEMARK OFFICE
CERTIFICATE OF CORRECTION

PATENT NO. : 6,869,924 B1
APPLICATION NO. : 07/330446
DATED : March 22, 2005
INVENTOR(S) : Yoshimura et al.

It is certified that error appears in the above-identified patent and that said Letters Patent is hereby corrected as shown below:

Col. 27, line 23, claim 2: "obtained in Step IV" should read --obtained in Step III--

Col. 27, line 28, claim 2: "obtained in Step lV" should read --obtained in Step IV--

Col. 27, line 34, claim 2: "peptide product as" should read --peptide product--

Col. 28, line 6, claim 4: "AVLFKTTYAKEICADPKQKWVQDSMDHLDKRTQTPKT" should read --AVIFKTIVAKEICADPKQKWVQDSMDHLDKRTQTPKT--

Col. 28, line 24, claim 4: delete duplicate "or conservative amino acid substitutions thereof."

Col. 28, line 53, claim 6: "an no acid sequence" should read -- an amino acid sequence--

Col. 30, line 15, claim 10: "appropriate cation change" should read --appropriate cation-exchange--

Signed and Sealed this

Twenty-second Day of August, 2006

JON W. DUDAS
*Director of the United States Patent and Trademark Office*